US011759247B2

(12) United States Patent
Condie et al.

(10) Patent No.: US 11,759,247 B2
(45) Date of Patent: Sep. 19, 2023

(54) SYSTEMS AND METHODS FOR DETERMINING AN ABLATION SCORE AND FOR PRE-ABLATION TESTING

(71) Applicant: BIOCOMPATIBLES UK LIMITED, Camberley (GB)

(72) Inventors: Catherine Condie, Shoreview, MN (US); Charles Houtz, Minneapolis, MN (US); Daniel Kollmann, Andover, MN (US); Oleg Mosesov, Maple Grove, MN (US)

(73) Assignee: BIOCOMPATIBLES UK LIMITED, Surrey (GB)

( * ) Notice: Subject to any disclaimer, the term of this patent is extended or adjusted under 35 U.S.C. 154(b) by 142 days.

(21) Appl. No.: 17/200,093

(22) Filed: Mar. 12, 2021

(65) Prior Publication Data

US 2021/0282835 A1    Sep. 16, 2021

Related U.S. Application Data

(60) Provisional application No. 62/989,311, filed on Mar. 13, 2020.

(51) Int. Cl.
*A61B 18/12* (2006.01)
*A61B 18/00* (2006.01)

(52) U.S. Cl.
CPC ............. *A61B 18/1206* (2013.01); *A61B 2018/00005* (2013.01); *A61B 2018/00577* (2013.01); *A61B 2018/00708* (2013.01); *A61B 2018/00791* (2013.01)

(58) Field of Classification Search
CPC ...... A61B 18/1206; A61B 2018/00005; A61B 2018/00577; A61B 2018/00708; A61B 2018/0079; A61B 2034/104
See application file for complete search history.

(56) References Cited

U.S. PATENT DOCUMENTS

| | | |
|---|---|---|
| 2003/0181965 A1 | 9/2003 | Levy |
| 2005/0171583 A1 | 8/2005 | Mosher |
| 2014/0378970 A1 | 12/2014 | Thompson |
| 2019/0262076 A1* | 8/2019 | Brown .................. A61B 18/02 |
| 2020/0345415 A1* | 11/2020 | Sharma ............. A61B 18/1233 |
| 2021/0153936 A1* | 5/2021 | Mosesov ............ A61B 18/1815 |
| 2022/0313346 A1* | 10/2022 | Qiu ........................ A61B 18/14 |

FOREIGN PATENT DOCUMENTS

WO    2016040056 A1    3/2016

OTHER PUBLICATIONS

International Search Report and Written Opinion for PCT/US2021/022110, filed Mar. 12, 2021, dated Jun. 14, 2021.
International Preliminary Report on Patentability for PCT/US2021/022110, filed Mar. 12, 2021, dated Sep. 6, 2022.

* cited by examiner

*Primary Examiner* — Linda C Dvorak
*Assistant Examiner* — Abigail Bock
(74) *Attorney, Agent, or Firm* — Faegre Drinker Biddle & Reath LLP

(57) ABSTRACT

Various aspects of the present invention are directed towards apparatuses, systems, and method that may include a tissue ablation system. The tissue ablation system may include an ablation device, an ablation generator, and a controller configured to initiate a pre-ablation procedure in a medium, and during the pre-ablation procedure monitor temperature data and/or power data.

20 Claims, 9 Drawing Sheets

SYSTEMS AND METHODS FOR DETERMINING AN ABLATION SCORE AND FOR PRE-ABLATION TESTING

CROSS REFERENCE TO RELATED APPLICATION

This application claims priority to Provisional Application No. 62/989,311, filed Mar. 13, 2020, which is herein incorporated by reference in its entirety.

FIELD OF INVENTION

The present invention generally relates to tissue ablation devices and methods of use.

BACKGROUND OF THE INVENTION

In the treatment of diseases such as cancer, certain types of tissues have been found to denature at elevated temperatures. These types of treatments, known generally as hyperthermia therapies, typically utilize electromagnetic radiation to heat cancerous tissue to temperatures above 60° C. while maintaining healthy tissue at lower temperatures where irreversible cell destruction will not occur. Microwave ablation is one of such treatments utilizing electromagnetic radiation to heat tissue.

Microwave tissue ablation is a less invasive procedure than surgical removal and may be in many situations when tumors are difficult to remove by surgery, for example when the tumor is relatively small, disposed close to a relatively small organ, or disposed close to a major blood vessel. The approach has been used in organs such as the prostate, heart, and liver, where surgical removal of tumors may be difficult to perform.

In order to effectively plan and optimize the procedure, it is desired that the ablation device causes predictably sized and shaped volumes of ablation. For this reason regularly shaped, predictable ablation volumes are preferred, and it is particularly preferred to produce spherical, or near spherical ablation volumes. An ablation device with predictably sized and shaped ablation volumes simplifies the surgical procedures and reduces the undesirable medical complications.

It is also desirable that ablation procedures are performed efficiently and that the ablation devices perform as expected during the procedures, so as to reduce the undesirable medical complications and achieve the desired ablation of the target tissue.

SUMMARY

In Example 1, a tissue ablation system includes an ablation device configured to provide energy to a target area; an ablation generator configured to provide power to the ablation device; a controller in communication with the ablation generator and being configured to initiate a pre-ablation procedure in a medium before an ablation procedure, during the pre-ablation procedure the controller is configured to cause an ablation generator to provide power to the ablation device, monitor temperature data, monitor power data representative of the power provided to the ablation device, and determine a condition of the ablation device based on the monitored temperature data and monitored power data.

In Example 2, the system of Example 1, the power delivered to the ablation device is between 1 and 20 watts.

In Example 3, the system of Example 1 or 2, the pre-ablation procedure includes delivering the power to the ablation device for 5 to 30 seconds.

In Example 4, the system of any of the preceding Examples, the medium is a tissue simulator.

In Example 5, the system of any of Examples 1-3, the medium is sterilized water.

In Example 6, the system of any of Examples 1-3, the medium is a tissue to receive an ablation procedure.

In Example 7, the system of any of the preceding Examples, the controller is further configured to cause a coolant to be provided to the ablation device.

In Example 8, the system of Example 7, the monitored temperature data is the temperature of the coolant.

In Example 9, the system of any of Examples 1-6, the monitored temperature data is a temperature of the medium surrounding the ablation device.

In Example 10, the system of any of the preceding Examples, the monitored temperature data is a temperature of the ablation device.

In Example 11, the system of any of the preceding Examples, the controller is further configured to conduct an ablation procedure.

In Example 12, the system of any of the preceding Examples, the ablation device includes a microwave ablation needle.

In Example 13, the system of any of the preceding Examples, further including a user interface configured to receive inputs regarding the pre-ablation procedure.

In Example 14, the system of any of the preceding Examples, further including a user interface configured to receive inputs regarding the ablation procedure.

In Example 15, the system of any of the preceding Examples, further including a second ablation device configured to provide energy to the target area.

In Example 16, a method of preparing an ablation device for an ablation procedure, the method includes inserting an ablation device into a medium; initiating a pre-ablation procedure before the ablation procedure, the pre-ablation procedure includes causing an ablation generator to provide power to the ablation device; monitoring temperature data; monitoring power data representative of the power provided to the ablation device; and determining a condition of the ablation device based on the temperature data and power data.

In Example 17, the method of Example 16, the power delivered to the ablation device is between 1 and 20 watts.

In Example 18, the method of Example 16, the pre-ablation procedure includes delivering the power to the ablation device for 5 to 30 seconds.

In Example 19, the method of Example 16, further including determining a power efficiency of the ablation device.

In Example 20, the method of Example 16, the medium is sterilized water.

In Example 21, the method of Example 16, the medium is a tissue to receive an ablation procedure.

In Example 22, the method of Example 16, further including providing a coolant to the ablation device.

In Example 23, the method of Example 17, the monitored temperature data is the temperature of the coolant.

In Example 24, the method of Example 16, the monitored temperature data is a temperature of the medium surrounding the ablation device.

In Example 25, the method of Example 16, the monitored temperature data is a temperature of the ablation device.

In Example 26, the method of Example 16, further including conducting an ablation procedure.

In Example 27, a method of preparing an ablation device for an ablation procedure, the method includes inserting an ablation device into a medium; initiating a pre-ablation procedure before the ablation procedure, the pre-ablation procedure includes causing a coolant pump to deliver coolant to the ablation device; causing an ablation generator to provide power to the ablation device; monitoring a temperature of the coolant; monitoring power data representative of the power provided to the ablation device; and determining a condition of the ablation device based on the monitored temperature and monitored power data.

In Example 28, the method of Example 27, the power delivered to the ablation device is between 1 and 20 watts.

In Example 29, the method of Example 27, the pre-ablation procedure includes delivering the power to the ablation device for 5 to 30 seconds.

In Example 30, the method of Example 27, further including determining a power efficiency of the ablation device.

In Example 31, the method of Example 27, the medium is sterilized water.

In Example 32, the method of Example 27, the medium is a tissue to receive an ablation procedure.

In Example 33, the method of Example 27, the monitored temperature data is a temperature of the medium surrounding the ablation device.

In Example 34, the method of Example 27, further including conducting an ablation procedure.

In Example 35, a tissue ablation system includes an ablation device configured to provide energy to a target area; an ablation generator configured to provide power to the ablation device; a controller in communication with the ablation generator and being configured to initiate a pre-ablation procedure before an ablation procedure, during the pre-ablation procedure, the controller is configured to cause a coolant pump to deliver coolant to the ablation device; cause an ablation generator to provide power to the ablation device; monitor a temperature of the coolant; monitor power data representative of the power provided to the ablation device; and determine a condition of the ablation device based on the monitored temperature and monitored power data.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF DRAWINGS

Advantages of the present invention may become apparent to those skilled in the art with the benefit of the following detailed description and upon reference to the accompanying drawings.

DETAILED DESCRIPTION

Figure 1A:
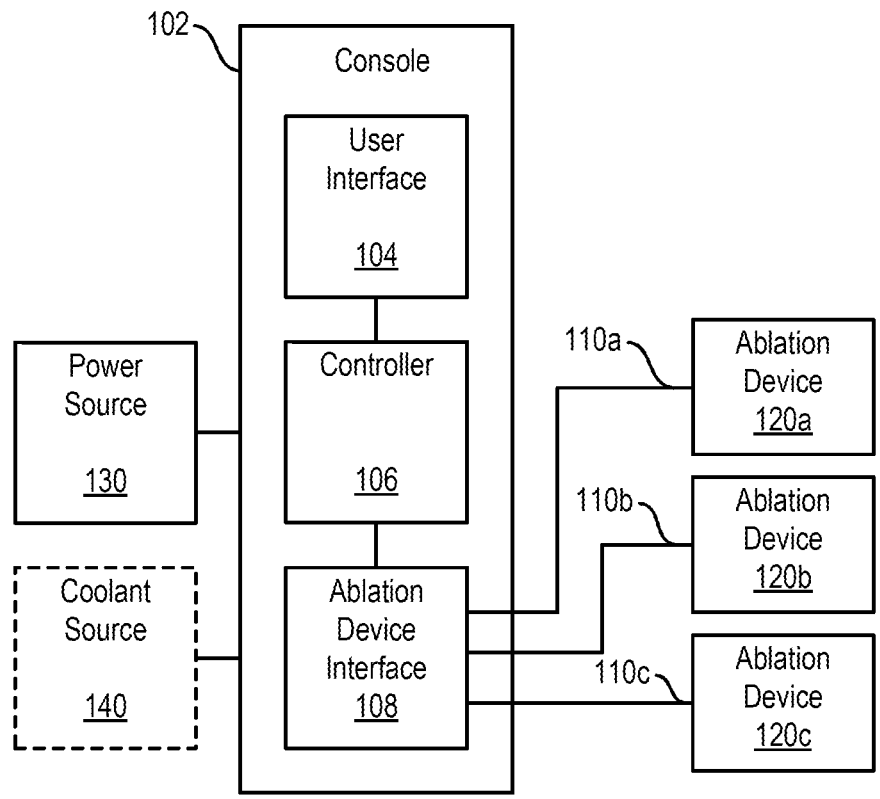
FIG. 1A shows a block diagram including components of a system for performing an ablation process according to one embodiment of the disclosure.

The size and dimension of an ablation area created by the microwave tissue ablation device is dependent, among other factors, on the type of microwave antenna. Clinicians may select a microwave antenna capable of generating an ablation region greater than the size and dimension of the target tissue and insert the microwave antenna such that the ablation region created by the microwave antenna includes the target tissue. Where the tissue to be ablated is larger than the size of the ablation volume produced by the device, more than one device may be used and the ablation volumes combined to cover the tissue to be ablated. The embodiments of the microwave tissue ablation device described herein may be used to create predictably shaped ablation regions, with reduced tailing which aids ablation planning and prevents damage to tissue outside the volume to be treated.

In some embodiments, ablation devices disclosed herein are microwave ablation devices configured to cause ablation by emission of microwave energy, which kills the tissue by heating. Typically, the devices are microwave ablation needles having microwave antennas such as those described herein.

In a further aspect, the invention provides a system for microwave ablation of tissue comprising one or more microwave ablation devices such as probes or needles as described herein, the microwave ablation device comprising a microwave antenna configured to transmit microwave energy to tissue, a microwave generator configured to provide microwave energy to the microwave antenna via a feedline, one or more power cables configured to connect the microwave generator to the microwave antenna of the ablation devices and to deliver microwave energy provided by the microwave generator to the antenna for the ablation of tissue.

Ablation devices such as those described herein can be configured to operate at powers of up to 150 watts and for periods of up to 20 minutes or more. The devices heat up during use due to resistive heating of the antenna and to energy reflected from the tissue and therefore typically at least the distal portion of the device including a distal portion of the feedline and the antenna will require cooling. Conveniently, in various embodiments, the whole feedline and antenna are cooled. Cooling the antenna prevents the device itself from becoming damaged and prevents tissue close to the antenna becoming over heated or charred. This alters the physical properties of the tissue, including its energy absorption and reflection characteristics and therefore reduces the efficiency of the antenna and may alter the ablation zone. In an embodiment the tissue ablation devices above therefore may additionally comprise a cooling system to cool the antenna and/or at least a portion of the feedline. Such cooling systems are typically configured to pass a cooling fluid such as a coolant (e.g., water) over at least a portion of the feedline and over the antenna. Typically, such systems comprise a coolant inlet and a coolant outlet which cooperate to pass a coolant over the antenna and optionally at least a portion of the feedline to cool the antenna and optionally at least a portion, preferably all, of the feedline. The antenna and feedline are typically in contact with the coolant.

In one option the cooling system comprises a coolant chamber surrounding the antenna and at least a distal portion of the feedline and having a coolant inlet conduit, configured to supply coolant to the coolant chamber and a coolant outlet conduit configured to carry coolant away from the coolant chamber, the coolant inlet and coolant outlet conduits configured to pass coolant over at least a portion of the feedline and at least a portion of the antenna.

FIG. 1A shows a block diagram including components of a system for performing an ablation process according to one embodiment of the disclosure. The system includes a console 102 including a user interface 104, controller 106, and an ablation device interface 108. In an embodiment, user interface 104 includes a display for presenting information to a user and an input device for receiving inputs from the user, such as via one or more buttons, dials, switches, or other actuatable elements. In an embodiment, user interface 104 comprises a touchscreen display that functions as both the display and the input device of the user interface 104.

According to an aspect of the invention, the ablation device interface 108 of the console 102 is arranged to interface with one or more ablation devices. In the embodiment of FIG. 1A, ablation device interface 108 interfaces with three ablation devices 120a, 120b, 120c via lines 110a, 110b, 110c, respectively. In an embodiment, a console 102 can interface one, two, or all three ablation devices (120a, 120b, 120c) individually or simultaneously. It will be appreciated that, while three ablation devices are shown in the embodiment of FIG. 1A, different aspects of the invention may include a console having an ablation device interface capable of interfacing with different numbers of ablation devices.

In an embodiment, a console includes an ablation device interface capable of interfacing with a single ablation device. In other embodiments, a console includes an ablation device interface capable of interfacing with two ablation devices, with three ablation devices, with four ablation devices, or with five ablation devices. In some examples, an ablation device interface can be configured to interface with any number of ablation devices.

According to certain aspects of the invention, a console can be used to operate any number of ablation devices up to the number of ablation devices supported by the ablation device interface. For example, a console having an ablation device interface capable of receiving three ablation devices simultaneously can be configured to operate one, two, or three ablation devices.

In an embodiment, lines 110a, 110b, 110c are configured to provide a coolant (e.g., from a coolant source 140) and ablation power (e.g., microwave signals) to ablation devices 120a, 120b, 120c, respectively. Lines 110a, 110b, 110c can be configured to provide a path for a coolant to be provided to a respective ablation device and a return path for receiving coolant from the respective ablation device after having traversed a coolant flow path within the ablation device.

According to an aspect of the invention, the controller 106 is configured to interface with the user interface 104 and the ablation device interface 108. In an embodiment, the controller 106 can be configured to receive one or more inputs via the user interface 104 and output one or more items via the user interface 104.

The controller 106 can be configured to control operation of one or more ablation devices (e.g., 120a, 120b, 120c) via the ablation device interface 108. In an embodiment, controller 106 can cause coolant to be provided to one or more ablation devices via the ablation device interface 108. The controller 106 can cause ablation power to be provided to one or more ablation devices in order to cause the ablation device to perform an ablation process. In an embodiment, the ablation power provided to an ablation device causes a microwave ablation device to emit microwave radiation. A power source 130 can provide electrical power used to generate the ablation power.

In an example, the controller includes one or more processors and memory comprising instructions for causing the one or more processors to be performed via the controller. In various embodiments of the invention, a controller may be implemented as one or more processors, such as one or more microprocessors, digital signal processors (DSPs), application specific integrated circuits (ASICs), field programmable gate arrays (FPGAs), programmable logic circuitry, or the like, either alone or in any suitable combination. A controller may also include memory that stores program instructions and related data that, when executed cause the controller to perform the functions attributed thereto in this disclosure. Memory may include any fixed or removable magnetic, optical, or electrical media, such as RAM, ROM, CD-ROM, flash memory, EEPROM, or the like. Memory may also include a removable memory portion that may be used to provide memory updates or increases in memory capacities. A removable memory may also allow image data to be easily transferred to another computing device. A controller may also be implemented as a System on Chip that integrates some or all components of a computer or other electronic system into a single chip.

Figure 1B:
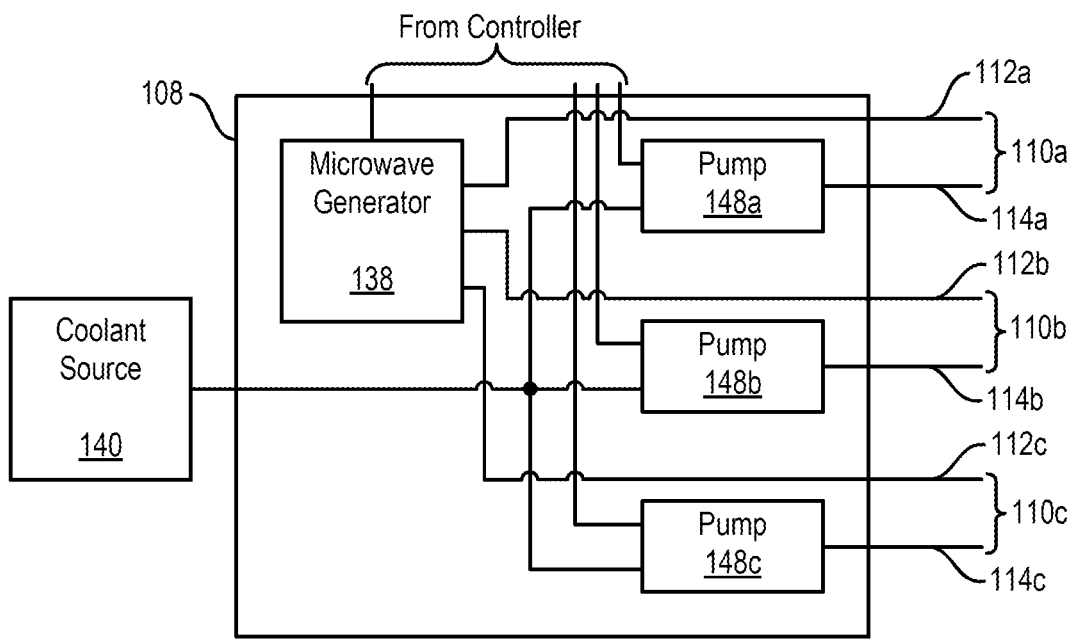
FIG. 1B shows a block diagram demonstrating operation of an ablation device interface for interfacing with an ablation device for performing an ablation process according to one embodiment of the disclosure.

FIG. 1B shows a block diagram demonstrating operation of an ablation device interface for interfacing with an ablation device for performing an ablation process according to one embodiment of the disclosure. In an example, an ablation device interface 108 includes one or more fluid pumps, each of the one or more fluid pumps (148a, 148b, 148c) being configured to pump a coolant to a respective ablation device. For example, as shown, pump 148a is in communication with coolant source 140, and can be configured to provide coolant to an ablation device (e.g., 120a) via a coolant line 114a. Such pump(s) can be controlled by the controller. The controller can be configured to control the flow rate of fluid provided from a pump (e.g., 148a) to an ablation device (e.g., 120a), including initiating the pump providing the coolant to the ablation device and stopping the pump providing the coolant to the ablation device.

In the example of FIG. 1B, the ablation device interface 108 includes three pumps 148a, 148b, 148c for providing coolant to a respective ablation device via coolant lines 114a, 114b, 114c, respectively. Coolant lines 114a, 114b, 114c can be included in lines 110a, 110b, 110c shown in FIG. 1A, respectively. In an embodiment, each pump is controlled by the controller and independently from the other pumps, for example, whereby any pump can operate independently of the operating status of the other pumps.

In another embodiment, each of pumps 148*a*, 148*b*, 148*c* comprises a peristaltic pump driven by a single motor controlled by the controller. In some such examples, each pump operates at the same rate defined by the motor, and coolant flows through any connected ablation devices via coolant lines 114*a*, 114*b*, 114*c*. The controller can adjust the flow rate of coolant through the ablation devices by controlling the speed of the motor.

In some examples, coolant provided to the ablation device is provided in a closed loop recirculation system, wherein coolant is received from the ablation device and returned to the coolant source 140. In an embodiment, coolant source 140 comprises a reservoir of coolant, such as sterile water, from which coolant is drawn, directed to one or more ablation devices via a coolant line, and returned to the reservoir from the one or more ablation devices via a coolant outlet line configured to carry coolant away from the ablation device. In some alternate examples, coolant outlet line(s) carry coolant away from the ablation device toward a waste system (e.g., toward a drain).

The ablation device interface of FIG. 1B includes a microwave generator 138 for generating and providing microwave signals to a microwave antenna in a microwave ablation device configured to transmit microwave energy to tissue. Providing microwave signals to the ablation device can include providing ablation power to the ablation device such that the device emits microwave radiation. Microwave generator 138 can provide microwave signals to ablation devices via power cable. In the embodiment of FIG. 1B, microwave generator 138 can provide microwave signals to up to three ablation devices via power cables 112*a*, 112*b*, 112*c*, respectively.

Power cables 112*a*, 112*b*, 112*c* are preferably coaxial cables which are preferably rated to at least 30 watts, preferably at least 100 watts, preferably at least 150 watts power. The cables may be cooled cables configured to be cooled by a coolant supply, preferably by circulating coolant along the cable between a cable coolant inlet and a cable coolant outlet. In some examples, coolant lines 114*a-c* provide coolant along power cables 112*a-c*, respectively. In an example configuration, the system comprises a cooling system and the cooling system is configured to cool both the cable and the microwave ablation device.

In some examples, the microwave generator is preferably configured to supply microwave energy to the antenna in one or more of the 915 MHz band (902 to 928 MHz), the 2.45 GHz band (2.402 to 2.483 GHz), or the 5.8 GHz band (5.725 to 5.875 GHz) range, preferably in the 2.45 GHz band, and most preferably at or about 2.45 GHz. The microwave generator may be configured to provide microwave energy to the antennas of up to 5 microwave ablation probes, preferably of one, two or three probes.

The microwave generator 138 can be configured to provide microwave signals prescribed by the controller 106. For example, in an example embodiment, the controller 106 can instruct the microwave generator 138 to provide particular microwave signals to a particular ablation device. The controller can be configured to designate a particular ablation magnitude (e.g., desired microwave power and/or energy emitted from ablation device, etc.), ablation duration, or other parameters, such as a duty cycle, phase shift, or other parameters associated with the microwave signal. In some examples, the microwave signal includes an electrical power (e.g., 90 W) delivered to the ablation device. The microwave signal can include an electrical signal including properties (e.g., electrical power, frequency, etc.) in order to cause the ablation device to emit microwave radiation having desired characteristics (e.g., microwave power radiated to surrounding tissue, etc.). The electrical signal can provide a desired ablation power to the microwave ablation device.

In an embodiment, the controller 106 can instruct the microwave generator 138 to apply microwave signals to each of a plurality of ablation devices. For example, with respect to FIG. 1B, the controller can instruct the microwave generator 138 to provide a first microwave signal to a first ablation device via power cable 112*a*, provide a second microwave signal to a second ablation device via power cable 112*b*, and provide a third microwave signal to a third ablation device via power cable 112*c*. In some such examples, the microwave generator 138 can provide such first, second, and third microwave signals simultaneously. Such signals can be the same signal or different signals. For example, in an embodiment, the same level of ablation power is provided by each of the first, second, and third microwave signals.

In some examples, the controller may be configured to control one or more of the following parameters: the output wavelength, the output power, the time period over which microwave energy is delivered to one or more of the antennas, the time period over which energy is delivered at an output power. Where the ablation device comprises a sensor, such as a temperature sensor, the controller can be configured to control any one or more of the parameters in response to a signal from the sensor (e.g., a temperature measurement). For example the controller may be configured to switch off the power to one or more of the antennas in response to an over temperature condition.

While shown in FIG. 1B as being implemented as a single microwave generator 138 configured to provide microwave signals to a plurality of ablation devices, in some examples, an ablation device interface 108 can include a plurality of microwave generators, each corresponding to a respective ablation device. In an embodiment, the controller 106 is in communication with a plurality of microwave generators and can be configured to cause the plurality of microwave generators to apply microwave signals to respective power cables (e.g., 112*a*, 112*b*, 112*c*) to provide such microwave signals to respective ablation devices.

FIG. 1B shows an example embodiment wherein three lines 110*a*, 110*b*, 110*c* can provide microwave signals and coolant to a respective three ablation devices simultaneously. In some aspects of the invention, microwave signals and coolant can be provided to a subset of lines 110*a*, 110*b*, 110*c*, for example, if fewer than three ablation devices are connected to the console 102. Further, in some aspects, microwave signals and coolant can be provided to a subset of lines 110*a*, 110*b*, 110*c* even if three ablation devices are connected to the console 102. For example, one or more such connected ablation devices can remain unused.

In an embodiment, controller 106 controls which ablation devices (e.g., which lines of 110*a*, 110*b*, 110*c*) receive microwave signals and coolant. In an aspect of the invention, the controller 106 can control aspects of the microwave signal, such as magnitude, frequency, duty cycle, duration, etc. of the microwave signal. In another aspect of the invention, the controller 106 can control aspects of providing the coolant to an ablation device, such as controlling a flow rate of the coolant, for example, by controlling operation of a respective pump. In an embodiment, for each ablation device, the controller controls aspects of both the microwave signal applied to an ablation device and aspects of providing the coolant to the ablation device. During operation, different ablation devices can each receive microwave signals and amounts of coolant independent of the signals and fluid received at other ablation devices, and can be the same as or different from microwave signals and amounts of fluid provided to other ablation devices.

While FIG. 1B shows an ablation device interface for interfacing with three ablation devices, it will be appreciated that a console according to different embodiments can include an ablation device interface capable of interfacing with a different number of ablation devices.

It will be appreciated that, while the block diagram of FIG. 1B shows an ablation device interface 108 including several components for interfacing with ablation devices, the components shown as being a part of the ablation device interface 108 are not necessarily contained within a single module or housing. Such components are grouped into the ablation device interface in that such components facilitate control of connected ablation devices by controller 106.

Additionally, while FIG. 1B shows an ablation device interface for interfacing with microwave ablation devices, it will be appreciated that similar ablation device interface concepts can be used to provide an interface between a controller and other ablation devices, such as RF ablation, cryoablation, or the like.

In an embodiment, the ablation device interface includes one or more ports configured to receive a portion of an ablation device, such as a cartridge having a fluid interface for connecting to a fluid line (e.g., 114a) and an electrical interface for connecting to a power cable (e.g., 112a).

Figure 2:
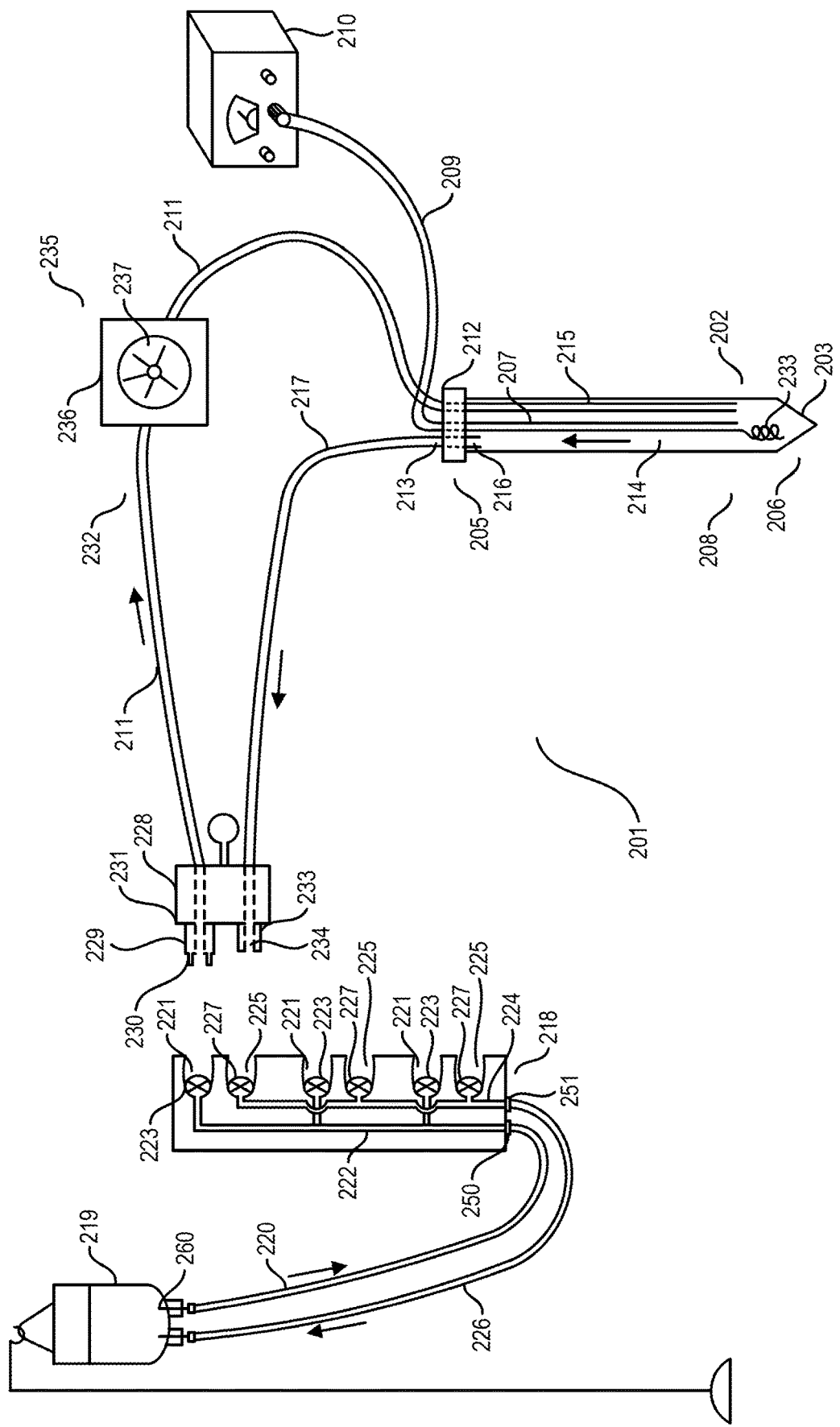
FIG. 2 is a simplified illustration of a cooling system according to the disclosure.

FIG. 2 is a simplified illustration of a cooling system according to the disclosure. The system 201 comprises an ablation device 202. In this case the microwave ablation device comprises a microwave ablation needle which is configured to deliver microwave energy to a patient's tissue to ablate the tissue.

The microwave ablation device 202 may have a tip 203 configured to penetrate tissue and an elongated shaft having a proximal end 205 and a distal end 206. The shaft encloses a coolant chamber 214 and a feedline 207, which may be a coaxial cable having an inner conductor, an outer conductor, and a dielectric therebetween (not shown in FIG. 2). The feedline of FIG. 2 comprises, distally, a radiating region 208 comprising a microwave antenna 204. The proximal end of the feedline 207 may be attached to a cable 209 (typically a coaxial cable) connecting the microwave ablation device 202 to a microwave generator 210 for providing microwave energy to the device. The cable may be releasably connectable, or, as in this case, permanently attached to the device. In some embodiments, as shown with respect to FIG. 1A or 1B, the microwave generator 210 may be housed within a console, such as console 102.

The device is provided with coolant via a device coolant supply line 211 which may be permanently attached to the device coolant inlet 212. In some embodiments, the device coolant supply line may, alternatively, be releasably connectable to the coolant inlet 212 such as via a Luer® type connector. The device coolant inlet 212 is in fluid communication with the device coolant outlet 213, via a series of coolant passageways 214, 215, and 216 configured to circulate coolant within the device. In this simplified representation, coolant enters the device through the coolant inlet tube 215, circulates through a coolant chamber 214 to cool the device, and leaves via the coolant outlet tube 216 and device coolant return line 217.

System 201 is provided with a manifold 218 which receives coolant fluid from a coolant fluid source 219, via a coolant system supply line 220. The coolant system supply line 220 may be permanently connected to the manifold 218 at the manifold fluid supply inlet 250 or it may be releasably connectable to the supply inlet 250, for example by a LuerLok® connector. The coolant fluid source may be, for example, an IV bag. The in-flowing coolant may be distributed to one or more manifold outlet ports 21, via a manifold inflow conduit 222. In an advantageous embodiment, and as illustrated in FIG. 2, flow of coolant out of the port 221 may be controlled by a manifold outlet valve 223. This valve may be normally in the closed position. In some embodiments, as shown with respect to FIG. 1A or 1B, the manifold 218 may be housed within a console, such as console 102.

The manifold 218 also comprises a manifold coolant outflow conduit 224 which provides a fluid connection between one or more manifold fluid inlet ports 225 and the coolant system return line 226. The coolant system return line 226 may be permanently connected to the manifold 218 at the manifold fluid return inlet 251 or it may be releasably connectable to the supply inlet 250, for example by a LuerLok® connector. In an aspect of the design, a manifold inlet valve 227 controls the flow through each inlet port and may also normally be in the closed state.

A supply coupling 229 is configured for connection to a manifold outlet port 221. The system may also comprise a return coupling 233 which is configured for connection to a manifold inlet port. In one aspect, the manifold outlet valve 223 may be configured to open upon connection of the supply coupling 229. In one approach, the supply coupling may comprise projections 230 which cause the valve to open upon connection of the coupling 229, to the port 221, but other arrangements are possible as discussed elsewhere herein.

A coolant circuit coolant inlet 231 on the supply coupling 229 is in fluid communication with the device coolant supply line 211 so that connection of the supply coupling 229 to the outlet port 221 places the cooling circuit 232 in fluid communication with the cooling fluid source 219.

A return coupling 233 may have a coolant circuit outlet 234 in fluid communication with the device coolant return line 217. The supply coupling 229 and the return coupling 233 can be arranged for simultaneous connection to the manifold outlet port 221 and inlet port 225 respectively.

A pumping portion 235 may be arranged in the device cooling circuit 232 and may be arranged in the supply line 211 for example, and is arranged to circulate the coolant through the microwave ablation device 202. In the system shown in FIG. 2, the pump is a disposable pump head 236 having pump vanes 237, permanently connected in the device coolant supply line 211 and adapted to be connected to a pump head drive (not shown). Alternative pumping portions may be used and are described elsewhere herein. In some embodiments, as shown with respect to FIG. 1A or 1B, the pumping portion 235 may be housed within a console, such as console 102.

Figure 3:
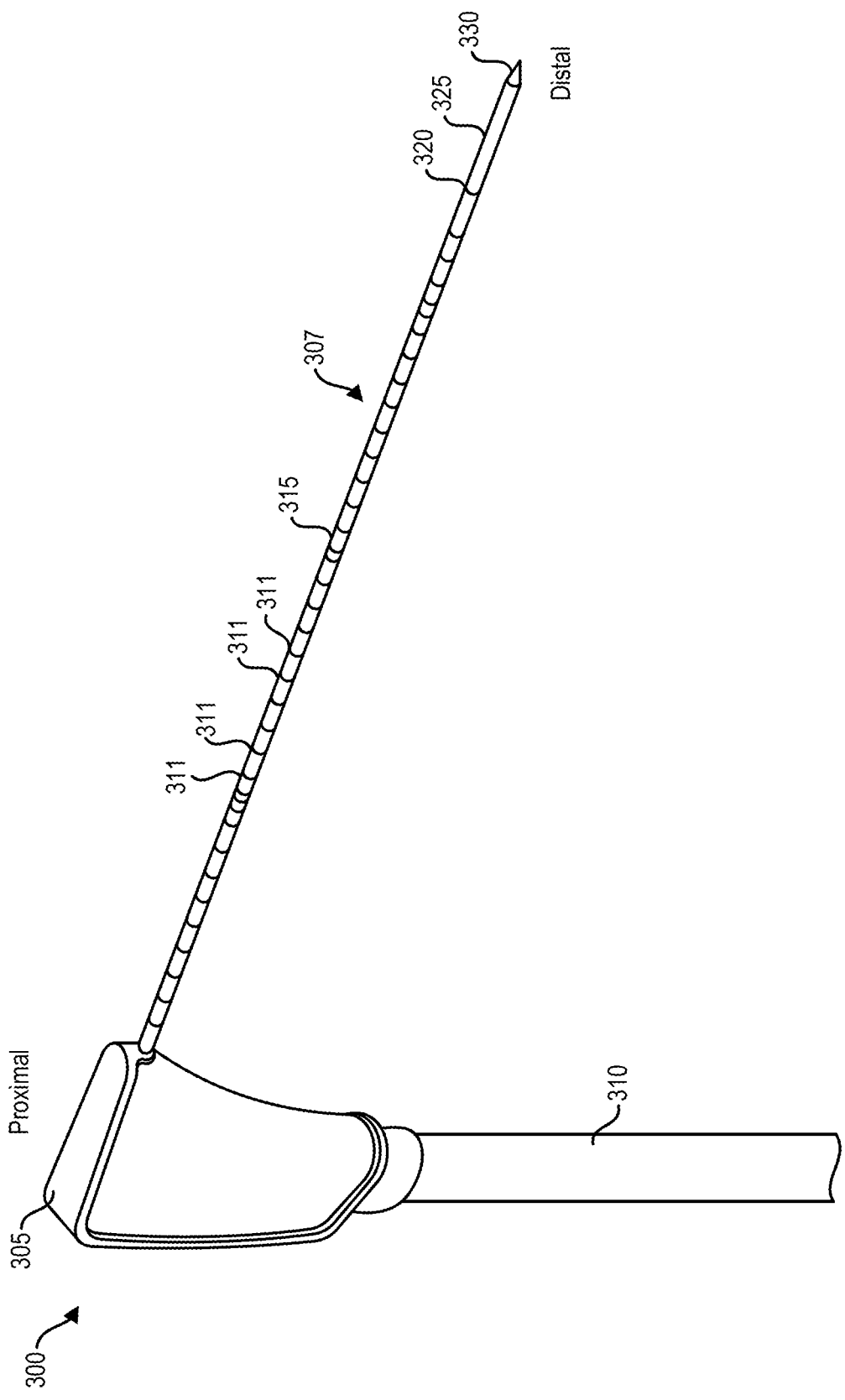
FIG. 3 is a perspective view of a microwave tissue ablation device with a handle according to one embodiment of the disclosure.

FIG. 3 is a perspective view of a microwave tissue ablation device 300 with a handle 305 according to one embodiment of the disclosure.

The microwave tissue ablation device 300 includes a handle 305. The handle 305 is configured to provide a firmer grip for a surgeon to handle the tissue ablation device 300. The handle 305 is further configured to house liquid manifolds for coolant circulation and coaxial connectors for powering the feedline.

The microwave tissue ablation device 300 includes a probe 307. The probe 307 is configured to be inserted into a patient's body for heating target tissue. In one embodiment, the probe 307 includes various ablation device components described elsewhere herein, such as the feedline, asymmetric dipole antenna, cooling system having inflow tubes and outflow tubes, etc. In an embodiment, the microwave antenna is configured to emit microwave radiation in a frequency band selected from the 915 MHz band (902 to 928 MHz) the 2.45 GHz band (2.402 to 2.483 GHz) and/or the 5.8 GHz band (5.725 to 5.875 GHz). The preferred wavelength is within the 2.45 GHz band and particularly the antenna is preferred to be configured to emit microwave energy at or about 2.45 GHz. The devices are configured to operate at up to 150 watts power supplied to the antenna.

The probe 307 includes a surface 315. The surface 315 is configured to be in contact with human tissue and is made with biocompatible materials. The device shaft is at least partially, metal, e.g., stainless steel, and includes markings 311, e.g., laser markings. The markings 311 are configured to inform the surgeon of the depth of the probe penetration into the body. It may comprise a lubricious surface layer such as PTFE, to aid insertion and prevent tissue sticking to the needle shaft while the needle is being inserted or extracted.

The shaft is typically cylindrical and is typically made of a biocompatible polymer, a biocompatible composite material, such as glass fiber reinforced polymer or carbon fiber reinforced polymer, ceramic or metal (such as stainless steel). The shaft is preferably made of ceramic or metal, but in a preferred embodiment the shaft comprises a metallic portion and a non-metallic portion. The non-metallic portion may be a biocompatible composite material, such as glass fiber reinforced polymer or carbon fiber reinforced polymer or ceramic, but is preferably ceramic due to its improved performance and strength. The ceramic is preferably an alumina or zirconia ceramic.

The shaft preferably terminates distally in a device cap. The shaft is preferably cylindrical. The feedline and antenna are preferably disposed within the device shaft. The device shaft typically extends from a proximal hub and terminates distally in a distal cap. The hub comprises electrical connections to electrical components of the shaft such as the feedline, and may also comprise coolant inlet and outlet connections, where necessary.

The diameter of the shaft is not limited, and is typically adapted for the intended purpose, for example for ablation needles, it is important to have a narrow needle to limit damage caused at insertion and to provide fine control of positioning, consequently the needle shaft is between 1.4 and 3 mm in diameter, preferably between 1.5 and 2.5 mm, particularly 2 to 2.5 mm.

The probe 307 of FIG. 3 includes an applicator cap 330. In an embodiment, applicator cap 330 is made of a biocompatible metal or a ceramic, e.g., preferably stainless steel or a ceramic. The applicator cap 330 can include a circular base and a distal tip (e.g., a trocar tip). The applicator cap 330 tip can include a sharp end disposed at a distal end of the applicator cap 330 and configured for penetration of tissue. The circular base can be configured to be sealed with a sheath of the probe 307 such that the interior of the probe 307 is fluidly isolated from the exterior of the probe 307.

The shaft may further comprise an echogenic region on the outer surface configured to be visible under ultrasound imaging. In one embodiment, this region comprises a coating comprising acoustically-reflective microspheres. The echogenic region extends at least to cover the region of the shaft radially outward of the antenna. The probe 307 of FIG. 3 includes an echogenic region 325 configured to be visible under ultrasound imaging and one embodiment, comprises a coating comprising acoustically-reflective microspheres.

Where the shaft comprises a metallic portion and a non-metallic portion, the joint between the two portions, where the metallic portion and the non-metallic portion abut, may be a point of potential weakness, especially where the non-metallic portion is ceramic, since ceramic is typically less flexible and more brittle than metals such as stainless steel. It is therefore preferred the shaft additionally comprises a resilient element between this portion and the metallic portion configured to provide resilience to the joint between the non-metallic (e.g., ceramic) portion and the metallic portion of the probe shaft in use.

The probe 307 further includes a region 320 configured to relieve strain on the probe induced during use, such as that caused by flexing of the shaft. This strain relief region is particularly useful when the distal portion of the probe sheath is ceramic. The strain relief region 320 is configured to provide the probe 307 added flexibility avoiding fracture of the probe 307 during a medical operation.

Although a resilient element may also be present between a non-metallic region and the cap, it is not necessary since the strains on the shaft at this point are lower. The resilient element may, for example, comprise a resilient annular spacer, which may be made of a resilient thermoplastic elastomer, such as polyether block amide (PEBA)—tradename PEBAX® or Vestimid®E (Evonik Industries) or a polyaryletherketone (PAEK) such as Polyetheretherketone (PEEK). The spacer is preferably shaped and configured to space apart the proximal end of the non-metallic portion from the distal end of the metallic portion. The resilient element preferably abuts the metallic portion on a proximal face and the non-metallic portion on a distal face. The resilient annular spacer typically extends radially outward to form a surface flush with the outer surface of the probe shaft. The radially inner portion of the annular spacer may be extended proximally and/or distally to provide an annular step configured to support the inner face of the the proximal end of the non-metallic portion and/or the distal end of the metallic portion. In one preferred embodiment, the annular spacer is extended proximally to provide an annular step configured to support the inner face of the distal end of the metallic portion, but does not extend distally. The device shaft may also comprise an adaptor sleeve to support the joint between the non-metallic portion and the metallic portion of the shaft. The adaptor may be configured to take account of any differences in thickness between the non-metallic portion and metallic portion of the shaft, such as to provide a smooth surface transition between the metallic and the non-metallic portions. It may be metallic, or non-metallic such as a thermoplastic elastomer, such as a PEBA PEBAX® or Vestimid®E or a PAEK such as PEEK. The adaptor is particularly important where the non-metallic portion is ceramic due to the thickness required for additional strength of the ceramic and the danger of flexing of the shaft causing cracking at this point. Conveniently the sleeve extends each side of the joint sufficiently to provide support for the joint and is typically positioned radially inward of the shaft, typically between the feedline and the inner wall of the shaft. The adapter sleeve is preferably metallic.

The resilient element and the adaptor sleeve together comprise a strain relief region. The resilient element and the adaptor sleeve may be a single piece or separate.

In one preferred embodiment, the strain relief region comprises a resilient element as described above, which comprises a resilient annular spacer shaped and configured to space apart the proximal end of the non-metallic portion from the distal end of the metallic portion, the spacer configured to abut the metallic portion on a proximal face and the non-metallic portion on a distal face, the spacer extending radially outward to form a surface flush with the outer surface of the probe shaft, the radially innermost portion of the spacer extending proximally to provide an annular step configured to support the inner face of the distal end of the metallic portion; the strain relief region additionally comprising an adaptor sleeve extending each side of the joint and radially inward of the annular spacer. Preferably the sleeve extends proximally of the annular spacer and is configured to be in contact with and support the inner face of the distal end of the metallic portion of the shaft; and preferably extends distally of the spacer and is configured to be in contact with and support the inner face of the proximal end of the ceramic portion of the shaft.

The microwave tissue ablation device 300 includes a housing 310. The housing 310 houses coaxial cables, fluid lines, electric lines, etc.

Figure 4A:
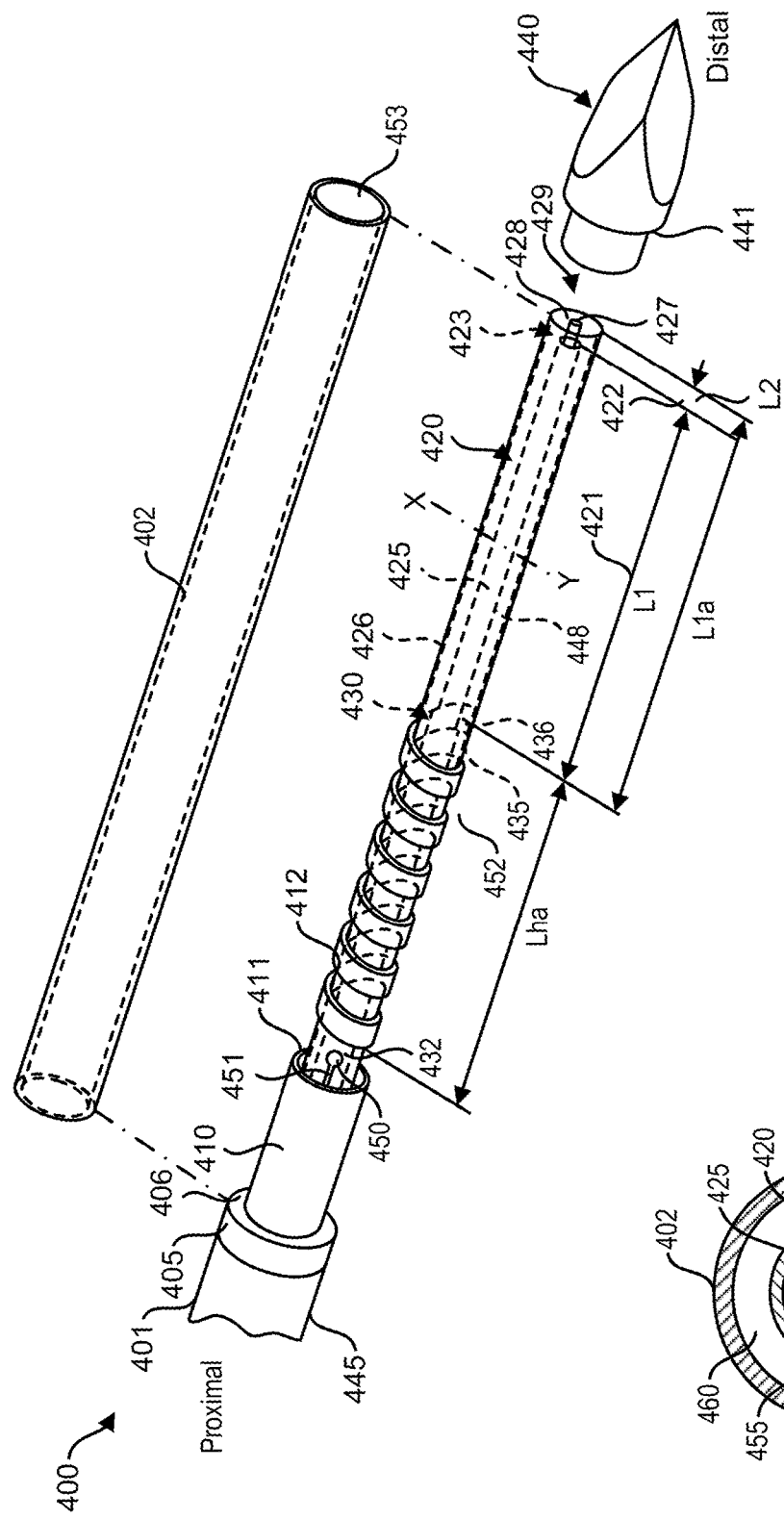
FIG. 4A is a perspective view of a microwave tissue ablation device 400 according to one embodiment of the disclosure.
Figure 4B:
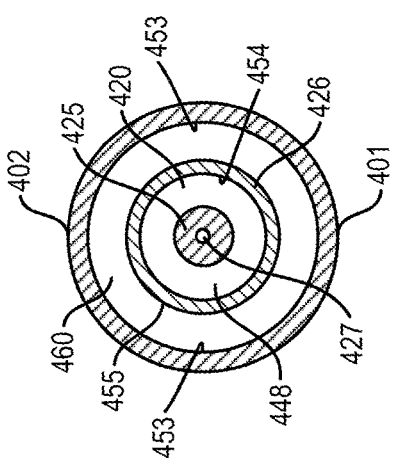
FIG. 4B is a sectional view across the line X-Y to illustrate one embodiment of the cooling features.

FIG. 4A is a perspective view of a microwave tissue ablation device 400 according to one embodiment of the disclosure. FIG. 4B is a sectional view across the line X-Y to illustrate one embodiment of the cooling features.

The tissue ablation device 400 of FIG. 4A has a shaft 401 having a metal portion 445 and a ceramic portion 402. The ceramic portion 402 extends from distal end 406 of a collar 405 to the base 441 of the cap 440. The ceramic portion 402 is shown separately from the shaft 401 in order to show the internal features of the device.

The tissue ablation device 400 includes a resilient element (e.g., collar 405), and an adaptor 410 to join the metal portion 445 to the ceramic portion 402 of the shaft. In devices of the invention, the adaptor takes up any difference in shaft thickness between the two portions and additionally acts to reduce flexing between the metal portion 445 and the ceramic portion 402. In devices of the invention, the resilient annular spacer between the ceramic portion and the metal portion of the shaft as shown here, acts to provide resilience to this region and to reduce the occurrence of fractures at this point due to strain on the shaft during use.

As described, for example, with respect to FIG. 1A or 1B, microwave energy generated by a microwave generator can be supplied to the antenna by a power cable which electrically connects the microwave generator to the feedline 432 of the antenna 452 within the device 400. The microwave ablation devices also have a shaft surrounding and typically coaxial with both the microwave antenna and at least a distal portion of the feedline. The shaft typically extends from a proximal hub to a distal cap.

The feedline preferably comprises an inner conductor, an outer conductor, and a dielectric disposed therebetween. The feedline may comprise a further dielectric or insulator that insulates the outer conductor from other parts of the device and acts as an outer insulator to the feedline, but it is not required in all embodiments. In some embodiments the further dielectric may be absent from the distal portion of the feedline, at least up to the junction point. The feedline may lack such a further dielectric within the device shaft, such as between a proximal feedline connector of a distal hub, and the junction point of the antenna. The feedline is typically a coaxial cable having a central conductor, surrounded by a first dielectric, or insulator, the first dielectric being surrounded by the second conductor, which may be covered by the further dielectric or insulator as described above. The inner conductor is typically the power conductor.

In the example of FIG. 4A, tissue ablation device 400 has an antenna 452 including a helical arm 412, and a linear arm 420. A distal end 435 of the helical arm 412 forms an electrical connection with the outer conductor 430 of the feedline 432 at a junction point 436. In some embodiments, the junction point is conveniently towards, or at, the distal most end of the feedline. The feedline 432 may extend beyond the junction point in order to provide suitable mechanical support to the electrical junction, but preferably it not extend by more than 5 mm and particularly not more than 1 mm beyond the junction point.

Typically the helical arm is in the form of a single conductor. The helical arm of the antenna may be in the form of a wire or a ribbon, but is typically a wire having a circular cross section or a ribbon. The helical arm is preferably in the form of a cylindrical conductor, having a helical gap running from its proximal to its distal end to give a helical conductor having a planar conductor surface curved about the feedline. The helical arm does not make any other contact with either the inner conductor or the outer conductor, except at the junction point.

In the example of FIG. 4A, the helical arm 412 extends proximally from the junction point 436 in a series of turns about the feedline 432 and so is coaxially disposed about the feedline. The helical arm 412 forms no other electrical contact with the inner conductor 427 or the outer conductor 430, except the junction point 436. The helical arm may be affixed to its substrate by an adhesive in order to hold it in place and to make assembly easier. The helical arm may be embedded within a matrix such as a polymer layer or coating in order to protect it, to insulate it from the other parts of the device, or to provide a seal.

In some embodiments, the helical arm is not coiled in direct contact with the feedline. It may, for example form turns at a position radially displaced from the feedline. The helical arm is preferably coiled about a substrate that supports it. Where the feedline comprises an outer insulator, this outer insulator may be the substrate for the helical arm, which may form turns around the outer insulator. Alternatively the helical arm may, for example, be coiled about a tubular substrate, such as a cooling tube positioned about the feedline.

In some embodiments, the total number of turns (N) is in the range of 1-12 but is not limited to integers. In preferred embodiments, N is typically from 4 to 8. For each complete helical turn, the axial distance is a pitch (P), which can range from 0.7-1.5 mm, preferably, the pitch ranges from 1-1.5 mm and in a preferred embodiment, the pitch (P) of the helical arm is from 1.2-1.25 mm. The number of helical loops (N), pitch (P) can affect the output of microwave energy, the shape of the emission field and the energy absorption spectrum. The judicious selection of each variable in combination can afford an ablation device with advantageous properties for tissue ablation.

In the example of FIG. 4A, the helical arm is coiled on a tube 426, which extends from the hub (not shown), through the metal portion 445 of the shaft to the tip 428 of the antenna 452. The electrical connection between the helical arm 412 of the antenna and the outer conductor of the feedline 432 passes through the tube at the junction point 436. In the illustrated example, the helical arm 412 has a length (Lha). In some examples, the overall length of the helical arm (Lha) can range from 1 to 18 mm, preferably the helical arm ranges from 4 to 10 mm. In a preferred embodiment, the helical arm ranges from 4 to 7 mm.

The linear arm 420 is an extension of the inner conductor 427 of the feedline 432 and is surrounded by a dielectric layer 425, except for the second portion 423, which is free of dielectric.

The linear arm of the antennas described herein is a conductor that is electrically connected to the inner conductor of the feedline and extends distally therefrom preferably on an axis co-axial with the helical arm and/or the feedline. The conductor is preferably in the form of a straight wire. In a particularly preferred embodiment, the linear arm includes a first, proximal, insulated portion and a second distal non-insulated portion. Typically, the first portion is surrounded by a dielectric and a second portion, distal of the first portion is free of dielectric. The second portion extends to the tip of the arm. The dielectric surrounding the first portion of the linear arm, preferably extends from the distal end of the feedline. In its simplest form, the linear arm of the antenna may be an extension of the feedline's inner conductor. The dielectric may then be an extension of the dielectric disposed between the central and outer conductors of the coaxial feedline.

Preferably, the linear arm and the helical arm of the antenna are coaxial with the shaft of the ablation device, and thus the linear arm is co-axial with and extends distally from, the helical arm. As shown, the linear arm 420 of the asymmetric dipole antenna of FIG. 4A has a length L1a. The linear arm includes a first portion L1 421 coated with an insulator, which is an extension of the first dielectric layer of the feedline 432 which is disposed between the inner conductor 427 and the outer conductor 430 and is not visible in this view. The linear arm 420 further includes a second portion 423 which has a length L2 422 and which is not coated with the insulator. In one embodiment, the second portion L2 422 is exposed to the circulating coolant.

In one aspect, the portion of the linear arm lacking dielectric is partially or completely inserted into the metal cap, but does not touch the cap. This can be achieved by creating an open pocket in the base of the cap into which this part of the antenna or a portion of it is inserted. The degree to which the exposed distal tip is inserted influences the shape of the distal portion of the energy field and hence the shape of the ablation zone.

Where the distance between the tip and cap is greater than 3 mm they are not considered to be sufficiently coupled to be useful in shaping the ablation, particularly at 2.45 GHz.

The linear arm 420 preferably has a length (L1a) of from 4 mm to 14 mm and preferably from 8 mm to 10 mm. The second, exposed portion 423 preferably has a length (L2) of from 0.1 mm to 2 mm, preferably from 0.3 mm to 0.5 mm.

Thus, in a preferred embodiment, the helical arm 412 of the antenna is in the form of a ribbon, having a length (Lha) of 1 to 18 mm and comprises 1 to 14 turns, the linear arm 420 of the antenna is 4 to 14 mm long and has a second, distal portion 423 lacking dielectric of 0.1 to 3 mm long, the portion lacking dielectric separated from the base of the cap by 0.2 to 3 mm.

In a more preferred embodiment, the helical 412 arm of the antenna is in the form of a ribbon, having a length (Lha) of 4 to 10 mm and comprises 4 to 8 turns, the linear arm 420 of the antenna is 7 to 10 mm long and has a second, distal portion 423 lacking dielectric of 0.3 to 0.5 mm long, the portion lacking dielectric separated from the base of the cap by 1 to 2 mm.

In a more preferred embodiment, the helical arm 412 of the antenna is in the form of a ribbon, having a length (Lha) of 4 to 6 mm and comprises between 3 to 5 turns. The linear arm 420 is 7 to 10 mm long having a second, distal portion 423 lacking dielectric 0.3 to 0.5 mm long, the portion lacking dielectric separated from the base of the cap by 1 to 2 mm, preferably by at or about 1.5 mm.

Where the shaft has a non-metallic portion (e.g., ceramic portion 402), the non-metallic portion preferably extends axially to cover the antenna and thus is at least co-extensive with the radiating portion of the antenna. In one embodiment, the non-metallic portion extends at least from the proximal most point of the helical arm to the distal end of the shaft. (e.g., the point of attachment of the tip of the device). The non-metallic portion extends axially and circumferentially such that the shaft is preferably non-metallic between the proximal and distal extent of the non-metallic portion.

A cap may be configured to seal the distal end of the device to prevent coolant leakage or tissue fluid penetration. The cap may be manufactured as a separate part and may be configured to be attached to the shaft. The cap is preferably configured to aid insertion into tissues and to penetrate the skin of a patient and so may, for example, come to a distal point, or be configured as a trocar. The cap 440 shown in FIG. 4A includes a trocar tip. The trocar tip of cap 440 can be made with stainless steel and/or ceramic.

In some examples, the cap may be made of any suitable biocompatible material such as a biocompatible polymer, composite, ceramic or metal such as stainless steel. Where the cap is metal, the cap and the distal end of the antenna (i.e. the distal end of the linear arm of the antenna) may be configured to be electromagnetically coupled. This can be done by adjusting the distance between the distal tip of the antenna and the cap so that they become electromagnetically coupled at the frequency and at the power at which the antenna is intended to operate. This effect can be used to tune the shape of the distal portion of the energy field generated by the antenna and hence the shape of the ablation zone. The cap and antenna need not, however be so coupled, i.e., the antenna may be electromagnetically decoupled from the cap. It is preferred that the tip and cap do not touch. In practice the gap between the tip and the cap is 0.2 mm or greater, particularly 0.2 mm to 3 mm and most preferably 1 to 2 mm. Most preferably it is at or about 1.5 mm.

The shape of the energy field and hence the ablation volume can also be influenced by the provision of a metallic sheath concentric with the feedline. The sheath is preferably cylindrical and extends over at least a portion of the feedline proximal to the antenna. The sheath may also extend over at least a portion of the antenna, but preferably it terminates at a point proximal to the distal most point of the helical arm of the antenna and does not extend over the antenna. Preferably the gap between the sheath and the distal most portion of the helical arm is at least 0.1 mm. The gap may be for example, between 0.1 to 2 mm or 0.1 to 1 mm, preferably it is at or about 0.5 mm. The sheath is preferably not placed on the outer surface of the shaft, but is preferably radially displaced from the feedline and coaxial with it. Preferably it is placed between the feedline and the inner wall of the shaft. In one arrangement, the metal sheath may be an adaptor sleeve as described elsewhere herein.

Preferably, a coolant chamber is defined between the inner walls of the device shaft. The chamber may be bounded distally by the cap and may be bound proximally by one or more proximal seals, which close the coolant chamber proximally. The one or more seals are preferably formed at the hub or at a point between the hub and the proximal portion of the helical arm of the antenna. The cooling system comprises at least one coolant inlet conduit configured to deliver coolant to the coolant chamber and at least one coolant outlet conduit to remove coolant from the chamber. The coolant inlet and coolant outlet conduits typically pass through the proximal seal. In one approach, the coolant inlet conduit is a coolant inlet tube configured to deliver coolant to a position adjacent to and radially outward of the antenna and or feedline. In this case, the coolant inlet tube is preferably disposed within the coolant chamber between the antenna and the inner wall of the shaft. Preferably it is displaced radially outward of the feedline.

In an alternative arrangement the cooling system comprises a coolant inlet conduit and a coolant outlet conduit, each conduit arranged about at least a portion of the feedline and a portion of the antenna. Each conduit arranged in the form of a helix, the coolant inlet conduit and the coolant outlet conduit being interdigitated one with the other to form a double helix. In one preferred arrangement, the cooling system comprises a pair of helical dividers arranged about the feedline and at least a part of the antenna in a double helix, each divider extending radially outward, towards the inner wall of the shaft and extending radially inward towards the antenna and/or the feedline such that the coolant inlet conduit and the coolant outlet conduit are formed between the two dividers and the coolant inlet conduit and coolant outlet conduit form a double helix. The dividers may be in the form of filaments or ribbons, or a combination of both. Where the dividers comprise a ribbon, the ribbon is preferably generally perpendicular to the inner shaft wall. The filaments may be formed of metal or of a resilient polymer. The dividers preferably extend to seal against the inner wall and at least a portion of the antenna and/or feedline.

The cooling system may additionally comprise a coolant mixing chamber in fluid communication with both the coolant inlet and coolant outlet conduits, such that the coolant inlet and coolant outlet are in fluid communication via the coolant mixing chamber. The coolant mixing chamber is preferably configured to allow coolant to pass over at least a portion of the antenna, particularly at least a portion of the linear arm of the antenna. The coolant mixing chamber is particularly configured to allow coolant to pass over the distal portion of the linear arm of the antenna and at least a portion of the cap.

Alternatively and preferably, the cooling system comprises a coolant chamber defined between the inner walls of the device shaft. The chamber may be bounded distally by the cap and proximally by a seal between the hub and the shaft, or at some point distal from the hub and between the antenna and the hub as previously described. The coolant chamber surrounds the antenna and at least a distal portion of the feedline.

In an embodiment, the cooling system further comprises a cooling tube disposed about the feedline, the cooling tube preferably extending distally about the feedline and preferably coaxial therewith. The cooling tube preferably divides the coolant chamber into a first cooling conduit 448 and a second cooling conduit 460, the first cooling conduit disposed between the feedline and the inner wall of the cooling tube and the second cooling conduit disposed between the outer wall of the cooling tube and the inner wall of the device shaft. The cooling tube preferably extends over the distal portion of the feedline and extends distally about at least a portion of the antenna, preferably the cooling tube extends at least to the tip of the linear arm of the antenna. A variety of materials are suitable for the cooling tube, but it is preferably non-metallic. Conveniently the cooling tube may be made of a thermoset polymer such as a polyimide or of a thermoplastic polymer resin such as polyethylene terephthalate (PET) or a fluropolymer such as polytetrafluroethylene (PTFE), or of a PAEK such as PEEK.

As described elsewhere herein, in the example of FIG. 4A, the helical arm is coiled on a tube 426. In an embodiment, the tube 426 defines a first cooling conduit 448 between the inner wall 454 of the tube 426 and the feedline 432 and a second cooling conduit 460 between the outer wall 455 of the tube 426 and the inner wall of the shaft 453. Coolant may be pumped through the space between the tube 426 and the feedline 432 to a mixing chamber 429 between the tube 426 and the cap 440 and returns in the space between the outside of the tube 426 and the ceramic portion 402 of the shaft, through the space 411 between the inside of the shaft and the adaptor 410 and back down the metal portion 445 of the shaft to the hub.

The helical arm of the antenna may be disposed within the first cooling conduit, for example, the distal portion of the feedline may comprise a second insulator as described above, and the helical arm of the antenna is wound directly about the feedline, the second insulator extending axially at least between the helical arm and the second conductor of the feedline. In this case, the cooling tube may extend to cover a portion of the helical arm, but preferably to cover the helical arm and a portion of the linear arm, but most preferably the cooling tube extends at least to the distal end of the antenna, such that the first cooling conduit extends at least to the tip of the antenna.

Otherwise the cooling tube extends to cover the distal portion of the feedline and a portion of the linear arm, but most preferably the cooling tube extends at least to the distal end of the antenna, such that the first cooling conduit extends at least to the tip of the antenna.

The cooling system may additionally comprise a coolant mixing chamber in fluid communication with both the first cooling conduit and the second cooling conduit, such that the first cooling conduit and the second coolant conduit are in fluid communication via the coolant mixing chamber. The coolant mixing chamber is preferably configured to allow coolant to contact a portion of the cap.

Either the first or the second cooling conduit may act as the coolant input conduit or coolant output conduit. The first and second cooling conduits are open at the distal end allowing the coolant to circulate through the coolant mixing chamber between the distal end of the cooling tube and the base of an applicator cap.

The cooling tube preferably extends proximally towards the hub. The first cooling conduit and second cooling conduits are in fluid communication with coolant input and output connectors of the hub, for the supply of coolant and discharge of coolant during use.

In a particularly preferred approach, the helical arm of the antenna, preferably in the form of a ribbon, is wound about the cooling tube. In this case, the helical arm is in electrical contact with the outer conductor of the feedline at the junction point and extends distally in a series of turns about the cooling tube as described above. In this case, the cooling tube preferably extends at least to the junction point of the antenna and feedline, preferably it extends to cover at least a portion of the linear arm, but most preferably the cooling tube extends to the tip of the linear arm, such that the first cooling conduit extends at least to the tip of the antenna. Preferably, the electrical contact between the distal end of the helical arm and the outer conductor of the feedline passes through the cooling tube.

In this approach it is preferred that the outer insulator does not extend over the distal portion of the feedline. Preferably, it does not extend over at least the portion which extends from a point on the feedline immediately proximal of the helical arm of the antenna to the junction point. The outer insulator may be absent from the entire feedline within the shaft of the ablation device.

In embodiments in which the cooling system comprises a cooling tube as described above, the helical arm may be either a wire or a ribbon, but is most preferably a ribbon. The helical arm is preferably in the form of a cylindrical conductor, having a helical gap running from its proximal end to its distal end to give a helical conductor having a planar conductor surface disposed about the feedline and preferably coaxial with it.

The cooling systems described herein pass a coolant (e.g., water) over the feedline and at least a portion of the antenna, preferably the whole antenna. It is not necessary to insulate the antenna from the coolant for normal operation. In some embodiments described herein, parts of the feedline are lacking an outer insulator surrounding the feedline. The feedline may be lacking an insulator between the hub and the junction point or its whole length within the device shaft. The helical arm of the antenna may also lack any insulation, particularly where it is wound about a cooling tube.

The ablation devices described herein may additionally comprise one or more temperature sensors, such as a thermocouple, to measure the temperature at points along the shaft. Typically a thermocouple may be located within the cooling system and configured to measure the temperature of the coolant or of other parts of the device such as the feedline or device shaft during operation of the device. The tissue ablation device 400 of FIG. 4A may include a temperature sensor 450 housed next to the internal adaptor 410 and having an electrical connection 451 via the hub to the control unit.

As described elsewhere herein, ablation devices such as those described herein typically comprise a proximal hub as discussed briefly above. The hub typically comprises connectors for connecting the feedline to an energy supply line and for connecting electrical devices within the device shaft to control systems. Such connectors may be permanent or demountable. The hub may also comprise a coolant manifold with input and output connectors for connecting the coolant input to a coolant supply and the coolant output to waste or recirculating system. The hub may also form part of a handle configured to provide a firmer grip for a surgeon to handle the tissue ablation device.

Figure 5:
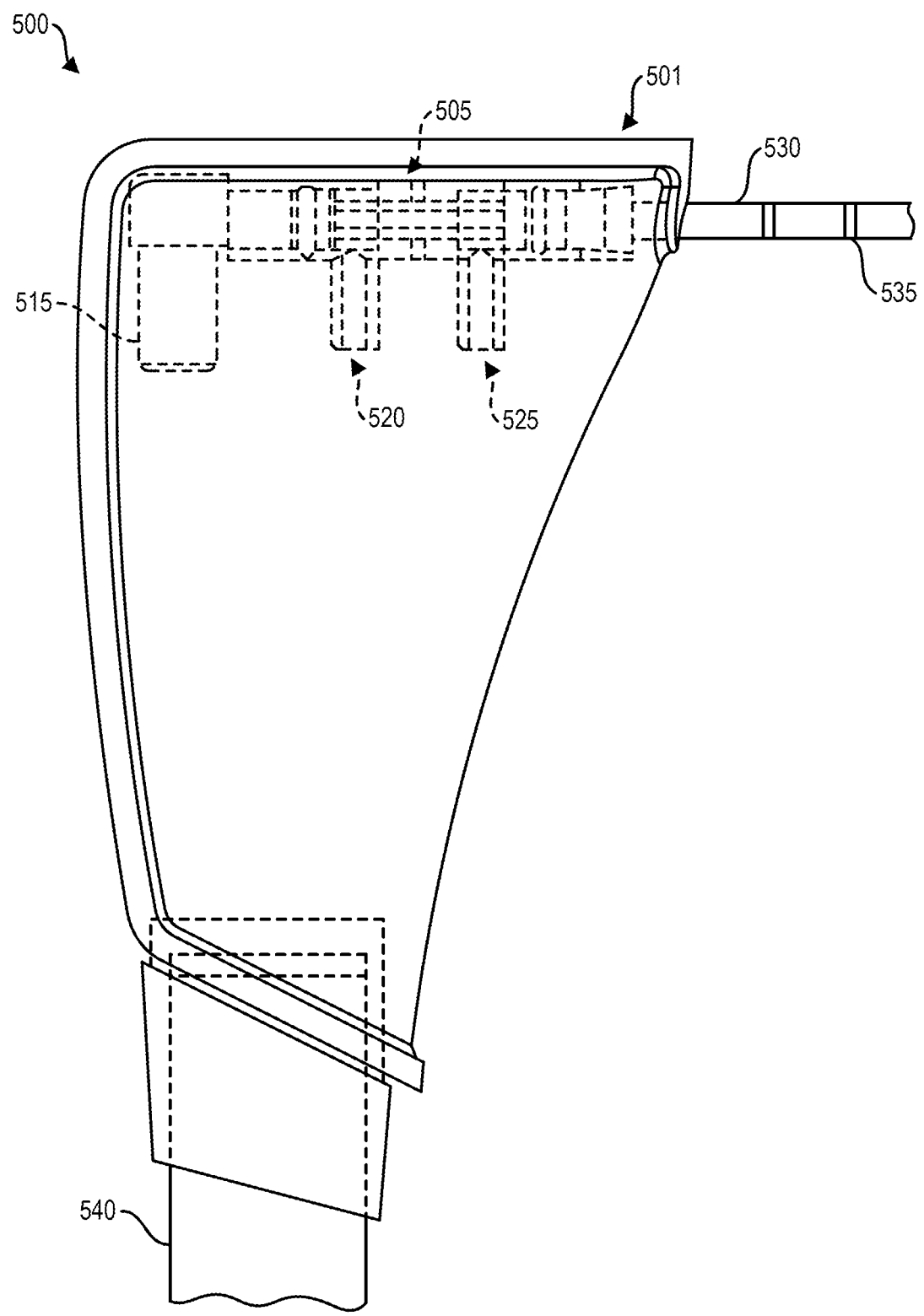
FIG. 5 is a side view of a microwave tissue ablation device according to one embodiment of the disclosure.

FIG. 5 is a side view of a microwave tissue ablation device according to one embodiment of the disclosure. The ablation device 500 includes a handle 501. The handle 501 houses a manifold 505.

The manifold 505 electrically connects the power source (not shown) and the tissue ablation probe 530 through the coaxial cable connector 515. The tissue ablation probe 530 includes markings 535 configured to inform surgeons of the depth of probe penetration during surgery.

The manifold 505 also fluidically connects the coolant source (not shown) and the tissue ablation probe 530. The manifold 505 includes a coolant inlet 520 and a coolant outlet 525. The coolant inlet 520 is fluidically connected to the coolant inflow conduit and the coolant outlet 525 is fluidically connected to the coolant outflow conduit.

The tissue ablation device 500 further includes tubular housing 540 that houses the electric wires and fluid tubes.

Figure 6A:
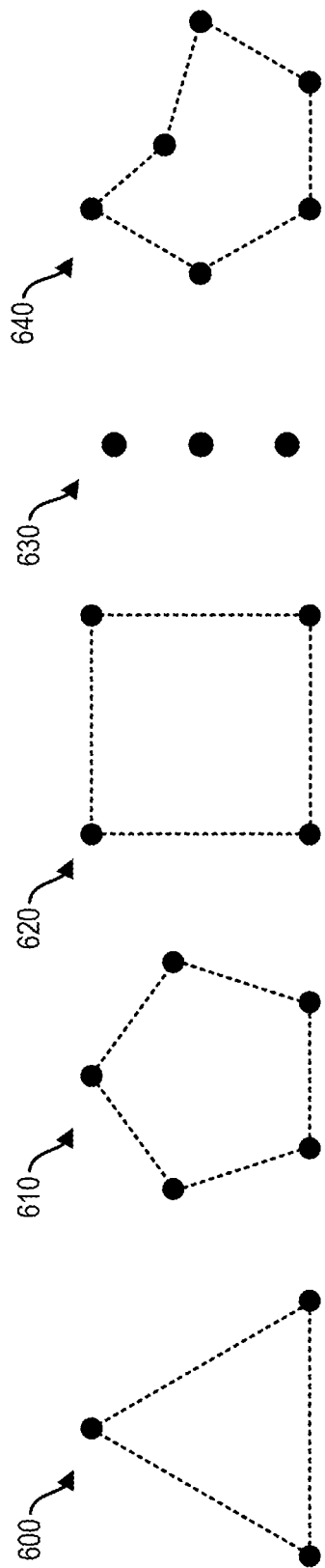
FIG. 6A shows a plain view of a plurality of microwave ablation needle configurations.

As discussed elsewhere herein, a plurality of ablation devices, such as tissue ablation device 300, can be used simultaneously to perform ablation processes. Such ablation devices may be arranged in a variety of ways. FIG. 6A shows a plain view of a plurality of microwave ablation needle configurations. In an example, microwave ablation devices can be positioned equidistant from each other, such as in arrangement 600. Needles can be arranged in a regular polygon formation, such as in arrangements 600, 610, and 620. Positioning the ablation devices equidistant from one another may advantageously provide an approximately symmetric net ablation volume formed by the plurality of ablation devices. Additionally, arranging the ablation devices in a regular polygon formation may provide an approximately spherical net ablation volume formed by the plurality of ablation devices. Alternatively, other arrangements, a plurality of devices arranged in a line such as in arrangement 630, or in an irregular shape such as in arrangement 640. Ablation devices can be arranged in a plurality of configurations to provide a desired ablation volume appropriate for a particular operation.

Figure 6B:
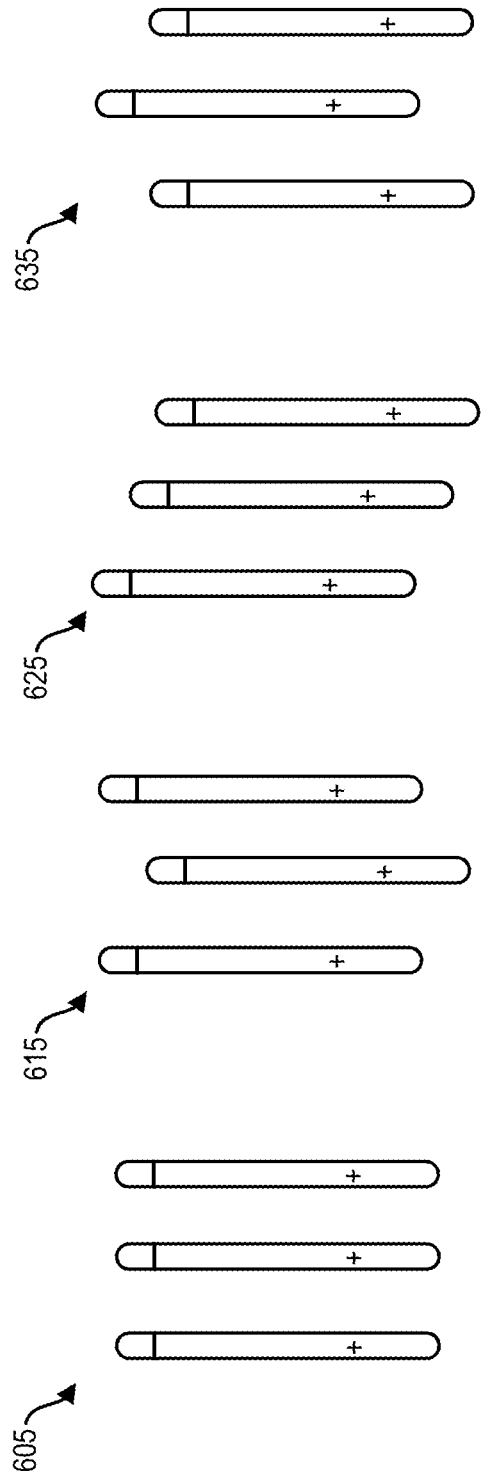
FIG. 6B shows an elevation view of a plurality of ablation devices at different depth arrangements.

In addition, such devices can be inserted to the same or different penetration depths. FIG. 6B shows an elevation view of a plurality of ablation devices at different depth arrangements. Ablation devices, such as microwave tissue ablation device 300, can be inserted to particular depths, for example, as gauged by markings 311. In some configurations, the devices are inserted to approximately the same depth, such as in arrangement 605. In other examples, devices can be inserted to different depths, such as in arrangements 615, 625, and 635. Similar to different plan arrangements, ablation devices can be arranged in a plurality of configurations to provide a desired ablation volume appropriate for a particular operation.

During operation involving one or more ablation devices, a console (e.g., 102) can actuate a pump (e.g., 148a) to cause a coolant to flow from a coolant source (e.g., 140) to each of the one or more ablation devices (e.g., 400). For each ablation device, coolant can flow through a coolant line (e.g., 114a), a coolant inlet (e.g., 520), a first cooling conduit (e.g., 448), a second cooling conduit (e.g., 460), and a coolant outlet (e.g., 525). In some examples, coolant line (e.g., 114a) provides a return path to receive fluid from the coolant outlet (e.g., 525), for example, in a recirculation system in which coolant is recirculated to the coolant source. In an embodiment, coolant can flow through such a flow path to provide cooling to the ablation device.

As described herein, a controller (e.g., 106), for example, within a console (e.g., 102) receiving the ablation device (e.g., 400) can be used to control the fluid flow through the ablation device as well as the microwave energy emitted from the ablation device.

Coolant can also act as a dielectric to couple microwave radiation emitted from a microwave antenna (e.g., 452) to surrounding tissue when the microwave ablation device is inserted in a patient. In an embodiment, coolant flows through the needle during a treatment ablation process at a treatment ablation flow rate. Coolant flowing through the needle at the treatment ablation flow rate can couple the microwave energy emitted from the needle to the tissue surrounding the needle and impact the penetration depth of the microwave energy into the tissue. Reducing the flow of coolant can reduce the coupling of the microwave energy to the surrounding tissue, resulting in a smaller ablation zone. Additionally or alternatively, reduced coolant flow can reduce the ability of the needle to draw heat away from tissue proximate the needle, resulting in more localized heating of tissue proximate to the needle compared to higher flow rates.

In some embodiments, a pre-ablation procedure is performed in order to ensure the ablation system is working properly. An exemplary pre-ablation procedure is shown with respect to FIG. 7. The ablation device may be initially tested in a medium separate from the patient's tissue, such as saline, sterilized water, or other sterilized medium, such as a solid or semi-solid material that mimics the dielectric properties of tissue, which are commonly referred to as tissue simulators or tissue phantoms (Step 710). It is also contemplated that a pre-ablation procedure could be performed in the patient's tissue, for example, by using a power level lower than the power levels typically delivered to a patient's tissue during an ablation procedure, such as the power levels discussed below.

Figure 7:
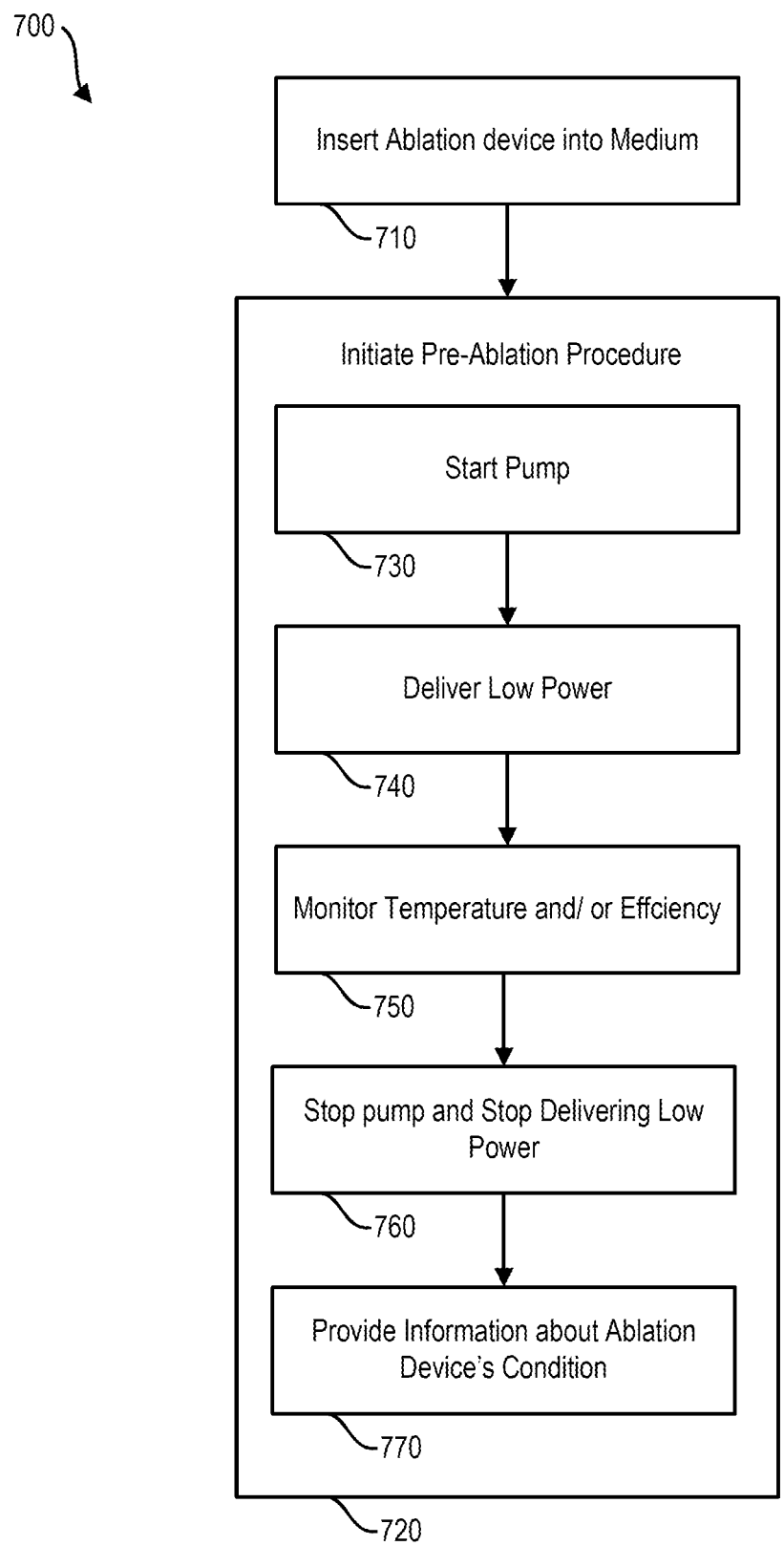
FIG. 7 is a block diagram detailing an exemplary pre-ablation procedure.

When the ablation device is placed in the suitable medium or tissue, a pre-ablation procedure may be initiated, such as the pre-ablation procedure shown as step 720 in FIG. 7. The pre-ablation procedure may be initiated manually by a user (e.g., physician) or automatically by the system, such as after contact with the suitable medium or tissue, or a certain duration after turning on. In embodiments where coolant is used, the pre-ablation procedure can start by initiating a pump (e.g., pumps 148*a-c*), for providing coolant to the ablation device (step 730). Pre-ablation procedure 720 can additionally comprise of delivering energy to the suitable medium (e.g., sterilized water) or tissue. In preferred embodiments, the power delivered to the suitable medium or tissue is lower than the power generally delivered to a patient's tissue, such as a power level of 1-20 W, however, power levels below 1 W and above 20 W have been contemplated. Preferably, a power level of 5 W is used for the pre-ablation procedure. The power level used for the pre-ablation procedure may depend in part on the measurement system being used, as lower power levels can be used with highly sensitive measurement systems.

It is understood that an ablation power level can be controlled in at least two different ways, by controlling the amplitude or by using duty cycling. For example, if it is desired to apply an average power level of 40 W, that may be accomplished by either setting the power level at 40 W, or by setting the power level at a higher value, 80 W, and implementing a 50% duty cycle. Both methods of controlling power level have been contemplated.

During pre-ablation procedure 720, power may be provided to the ablation device for a set duration, such as 5-30 seconds, however, other durations have been contemplated such as less than 5 seconds or more than 30 seconds. Preferably, the pre-ablation procedure has a duration of 10 seconds. The duration may be determined by the ablation system, such as with a default predetermined duration. In some embodiments, a user may select the predetermined duration such as by selecting from a list or inputting a specified duration. The duration may also be based on a user selecting the power level provided to the ablation device, such as by an actuation (e.g., button, switch, touch interface). The duration may be additionally dependent on a total amount of power (e.g., energy) provided to the ablation device.

The pre-ablation procedure may be used to determine whether the ablation system is functioning properly prior to its use in an ablation procedure. It may be advantageous for a user or physician to determine if any problems exist with the console, ablation device, or set-up of the system prior to use of the ablation system on a patient (e.g., via the ablation procedure) to ensure the ablation procedure is properly performed. An improper ablation procedure may result in an incomplete ablation, or discomfort or harm to the patient.

Pre-ablation procedure 720 may additionally comprise monitoring data, such as temperature data and/or power data (step 750), to determine whether the ablation system is functioning properly. The temperature data may be representative of the temperature of the ablation device or the temperature of the medium or tissue surrounding the ablation device. In embodiments where coolant is used, the temperature data may also be representative of the coolant temperature within the ablation device. With respect to temperature data, it may be desired for the ablation device or coolant to be maintained within a temperature range, such as above 15 F and lower than 25 F. Additionally, variances in temperature may be used to determine the functionality of the ablation system, such as sudden changes in temperature may be an indication of bubbles in the coolant. Rapid increases in coolant temperature after power is initially delivered to the ablation device may also indicate that the system is not functioning properly.

With respect to power data, the power data may be used to calculate power efficiency, such as the ratio of the reflected power to the provided power. As similarly shown above, it may be desired to have the efficiency be within a threshold range, such as within the range of 60% to 80%. Preferably, the power efficiency is above 75%. Additionally, variances in efficiency may be used to determine the functionality of the ablation system. For example, drastic changes in efficiency may indicate loose connections in the system or air bubbles in the coolant if used. Additionally or alternatively, the provided power and reflected power may be used to determine the functionality of the ablation system, such as with using thresholds and variances as discussed herein. Changes in efficiency may also indicate that the wrong coolant is present, no coolant is present, the ablation device is not functioning properly, the set-up of the pre-ablation procedure is incorrect, or the ablation device is not properly positioned within the medium or tissue.

After power is provided to the ablation device for the desired duration, and/or the desired amount of power is provided, the power provided to the ablation device is stopped (step 760). Additionally, step 760 may comprise stopping the pump (e.g., pump 148) such that coolant is no longer provided to the ablation device in embodiments using a coolant system. Alternatively, the pump may continue pumping coolant through the ablation device after the pre-ablation procedure, such that coolant is continuously provided between the pre-ablation procedure and the ablation procedure.

Information about the ablation device's condition may be provided after stopping power provided to the ablation device (step 770). In some embodiments, information about the ablation device's condition may be provided throughout the pre-ablation procedure. The information regarding the ablation device's condition may comprise the temperature data and/or power data collected during the pre-ablation procedure. Information may be provided to the user via a user interface (e.g., graphic user interface 900) and/or stored in memory for later use. Additionally or alternatively, the information may comprise a notification to inform the user on whether or not the ablation device is functioning properly. The notification may be displayed on a display, may be an LED (e.g., green for functioning properly, red for functioning improperly), or any other notification system known in the art.

The pre-ablation procedure may be performed at any time such as during a routine maintenance check, upon manipulating components of the ablation system, upon instructions inputted by a user, or upon turning on the ablation system. In preferred embodiments, the pre-ablation procedure is performed before conducting an ablation procedure, such as ablation procedure 800 which is described with respect to FIG. 8.

With respect to ablation procedure 800, initially the ablation system may determine the ablation procedure parameters (step 810), such as by receiving inputs regarding ablation parameters (step 810). Ablation procedure parameters may be target area dimensions, the positioning of the one or more ablation devices, including the geometry of the devices within the tissue if more than one device is being used, a predetermined ablation duration, and/or a predetermined amount of energy. The ablation system may receive inputs regarding the ablation procedure parameters via a user interface such as with adjustable parameters 940 of graphic user interface (GUI) 900. With respect to adjustable parameters 940, the ablation system may receive inputs regarding the diameter of the target area (e.g., 3.5 cm) and the arrangement of the ablation devices (e.g., arrangements shown in FIGS. 6A and 6B). The ablation system may also provide suggested ablation parameters in response to received inputs regarding the target tissue area or dimensions. These parameters may include recommended ablation power levels, total energy amount, and/or ablation duration for the ablation procedure.

After determining the ablation procedure parameters, the ablation system may initiate delivering ablation power to the target area (step 820). Step 820 may be performed automatically, such as after determining the ablation procedure parameters in step 810, or may be performed manually, such as by the ablation system receiving an input from a user. In embodiments wherein a coolant system is used, the ablation procedure may additionally start one or more pumps, such as pumps 148a-c, for providing coolant to the ablation device.

Similar to pre-ablation procedure 700 and other ablation procedures discussed herein, the ablation system can monitor the ablation power within the ablation system, as depicted in step 830. Monitoring the ablation power may comprise monitoring the provided power and/or the reflected power.

Additionally or alternatively, the duration may be determined based on whether or not an energy goal has been met (e.g., predetermined amount of energy). As shown in step 840, the ablation device may continue delivering ablation energy until the energy goal is met. Determining whether or not the energy goal is met may comprise monitoring the provided power and/or the reflected power of the ablation device. Ideally, all of the power provided to the ablation device will be delivered to the target area. However based on the power level parameters (e.g., amplitude, frequency, etc.), composition of the target area (e.g., tissue type, water content, etc.), type of ablation device used, proximity to other mediums (e.g., bones, air pockets, additional ablation devices, auxiliary devices, etc.), or the like may result in a portion of the power provided to the ablation device being reflected back. Additionally or alternatively, poor coupling of the ablation device and the surrounding tissue can lead to power reflection within the ablation device.

The ablation system may be able to determine the provided power and/or the received power of the ablation device, such as by receiving information regarding the provided power and/or the reflected or coupled power. In some embodiments, the ablation device may comprise a directional coupler. The directional coupler may be used to measure delivered power as well as received power on the ablation device. Additionally or alternatively, other devices may be used to determine received power, such as directional couplers on additional ablation devices or an antenna configured to receive power. When using a directional coupler or similar devices, reflected power may be determined by monitoring the received power (e.g., $S_{11}$ of a directional coupler). In such embodiments, the $S_{11}$ signal may be representative of power reflected back by the ablation needle and not received by the tissue. Additionally, monitoring the reflected or coupled power may be used to determine the delivered power. In some embodiments, it is assumed that any power not reflected or coupled is delivered power.

In addition to monitoring the provided power and received power, step 830 may additionally comprise measuring the temperature during the ablation procedure. As discussed herein, the ablation system may comprise one or more temperature sensors, such as temperature sensor 450. The temperature monitored by the one or more temperature sensors may be representative of the ablation device or the tissue surrounding the ablation device. Additionally or alternatively, the temperature monitored by the one or more temperature sensors may be representative of the temperature of coolant in some embodiments.

After the desired amount of energy is provided (e.g., energy goal met in step 840) or power is provided to the ablation device for a desired duration, the power delivered to the ablation device is stopped (step 860). Additionally, the pump (e.g., pump 148) may be stopped such that coolant is no longer provided to the ablation device if coolant is being used. Alternatively, coolant may be provided after the ablation procedure, such as if another ablation procedure is to be performed soon after.

The ablation system may monitor the tissue temperature after power is no longer provided to the ablation device as shown in step 870. The tissue temperature may be monitored by a sensor located on the ablation device or by an external temperature measuring device, such as by a temperature sensor (e.g., temperature sensor 450), or by monitoring the temperature of the coolant, which is reflective of the tissue temperature. The post ablation temperature may be representative of how well the tissue surrounding the ablation device has been ablated. For example, if not enough ablation power was provided, the temperature post ablation may show that the temperature of the surrounding tissue was not raised to an acceptable temperature to fully ablate the target area. For example, typically, the tissue temperature should be raised above 50° C., and preferably above 60° C.

Figure 8:
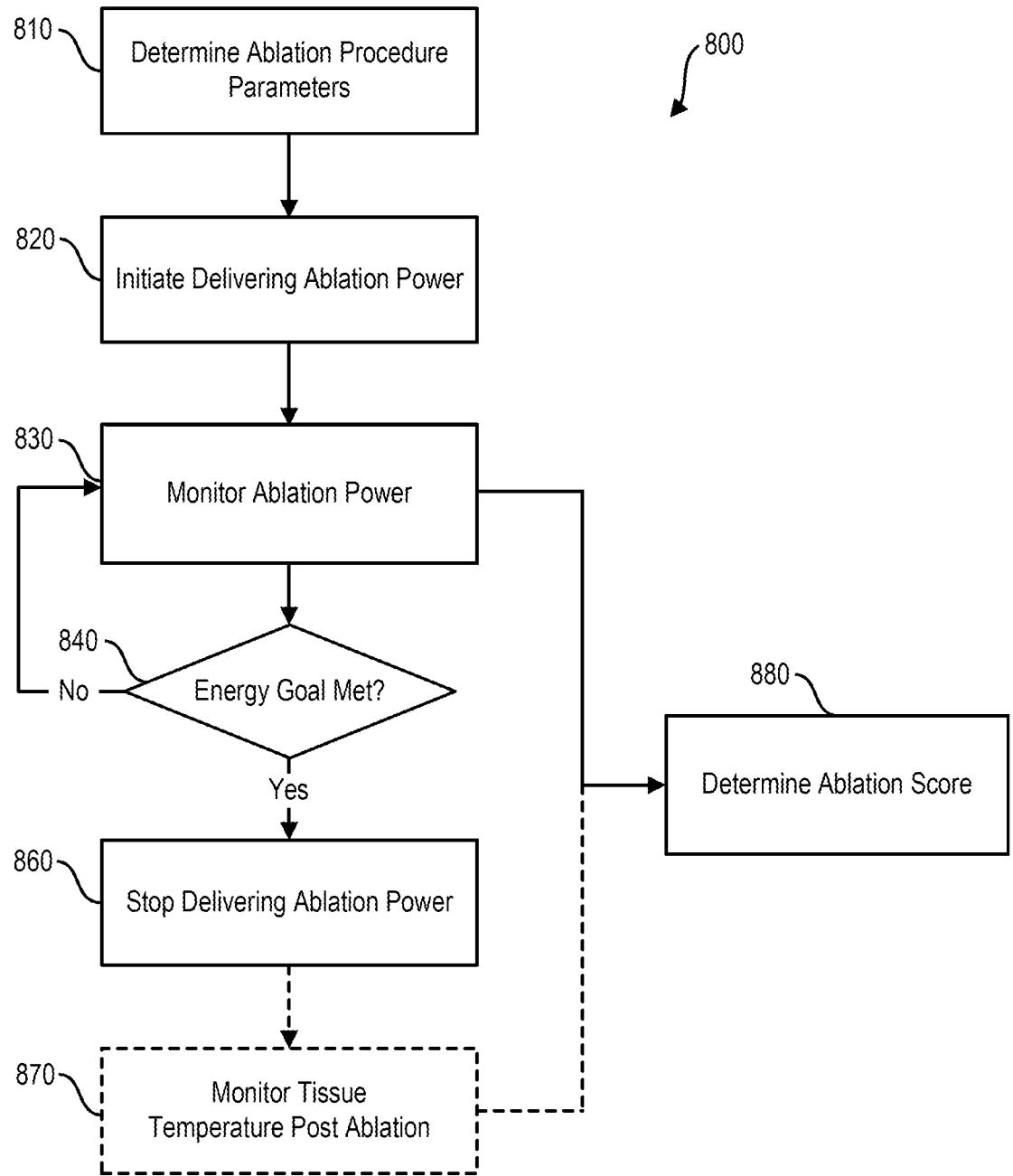
FIG. 8 is a block diagram detailing an exemplary ablation procedure.

Values monitored throughout the ablation procedure may be used to calculate an ablation score (step 880). As shown in FIG. 8, both the monitored power and temperature values may be used to calculate the ablation score. The ablation score can be representative of the quality of the ablation at the end of the ablation procedure. The ablation score may be additionally influenced by other values, such as information stored during a pre-ablation procedure. In some examples, values monitored throughout the ablation procedure are unevenly weighted when calculating the ablation score. For example, the ablation score may be calculated by using the monitored power, such as by the power efficiency during the ablation procedure. Additionally or alternatively, the ablation score may be influenced based on whether or not thresholds are reached. For example, an ablation procedure may receive a poor ablation score if a required post ablation temperature is not reached, regardless of the performance of other monitored/calculated values (e.g., power efficiency).

The ablation score may be stored along with monitored values, ablation procedure parameters, pre-ablation procedure information, ablation system used and/or the location of the target area (e.g., type of tissue in the patient). Stored ablation scores may be used to determine the effectiveness of ablation procedures to determine the effectiveness of ablation procedures in order to perform effective or more effective ablation procedures in the future.

Figure 9:
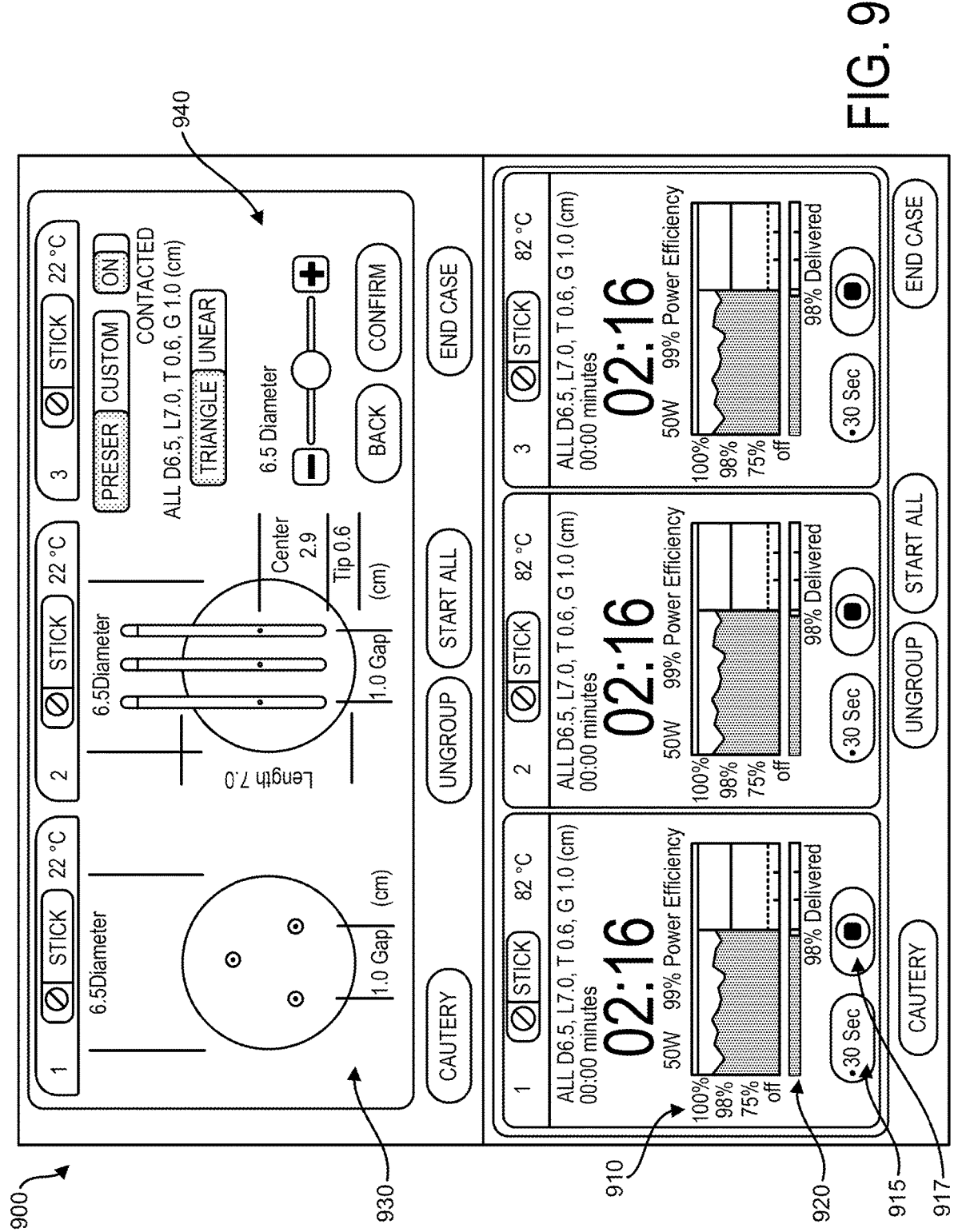
FIG. 9 shows a GUI which can be used for an ablation procedure.

FIG. 9 shows an example GUI 900 for an ablation system. In some embodiments, an overall efficiency value is displayed. Such an efficiency value can be presented in real-time during ablation and represent the efficiency of the ablation thus far (e.g., 99% efficiency with 2.16 left as shown in FIG. 9). Smaller increments of efficiency may also be recorded and displayed, such as depicted in graph 910. During an ablation procedure, efficiency values may be calculated once every second. Graph 910 displays the changes in efficiency over time. In the ablation procedure depicted in graph 910, the efficiency wavers between 98% and 100%. In some examples, GUI 900 may include both an efficiency vs. time plot (e.g., graph 910) as well as an overall efficiency value. GUI 900 may additionally display a graphical representation of the delivered energy, such as bar graph 920 shown underneath graph 910.

The ablation system can also be configured to convert the delivered power and/or power efficiency into a delivered energy and/or energy efficiency value. For example, the integral of power delivered over time can be computed to determine a total energy delivered. The delivered energy value can be compared to a provided energy value to determine energy efficiency.

GUI 900 may additionally provide a graphical representation of the ablation procedure, such as the shape and size of a theoretical target area based on a positioning of the one or more ablation devices to be used. With respect to the ablation procedure shown on GUI 900, display 930 displays three ablation devices positioned with a 1.0 cm gap between them which is predicted to provide an elongated spherical target area having the dimensions of 6.5×6.5×7.0 cm. The predicted target area shape may be calculated based on the ablation procedure parameters. Additionally, display 930 may provide the position of the predicted target area relative to the one or more ablation devices. In the ablation procedure shown on GUI 900, the center of the target area is positioned 2.9 cm from the tip of the ablation devices and the bottom of the target area is positioned 0.6 cm from the tip of the ablation devices.

The ablation system may receive inputs regarding ablation parameters, such as the target area dimensions, the positioning of the one or more ablation devices, a prescribed ablation duration, and/or a prescribed amount of power/energy. The ablation system may receive inputs regarding the ablation procedure parameters via a user interface such as with adjustable parameters 940 of GUI 900. With respect to adjustable parameters 940, the ablation system may receive inputs regarding the diameter of the target area (e.g., 6.5 cm) and the arrangement of the ablation devices (e.g., arrangements shown in FIGS. 6A and 6B).

During an ablation procedure, the ablation system may receive inputs, such as inputs from a user interface (e.g., adjustable parameters 940). Received inputs may comprise an input for adjusting the current power level to provide more or less power to the target rea. Additionally or alternatively, the ablation system may receive inputs to adjust the duration of the ablation procedure. For example, the user interface may be configured to receive inputs to increase the total ablation duration (e.g., +30 seconds as shown in 915) or receive inputs to decrease or terminate the ablation procedure (e.g., 917).

Various non-limiting examples have been described. These and others are within the scope of the following claims. Additionally, while the invention is susceptible to various modifications and alternative forms, some specific embodiments thereof are shown by way of example in the drawings. The drawings may not be to scale.

The invention claimed is:

1. A method of preparing an ablation device for an ablation procedure, the method comprising:
   inserting an ablation device into a medium;
   initiating a pre-ablation procedure before the ablation procedure, the pre-ablation procedure comprising:
      causing an ablation generator to provide power to the ablation device;
      monitoring temperature data;
      monitoring power data representative of the power provided to the ablation device;
      determining a condition of the ablation device based on the temperature data and power data; and
      providing a coolant to the ablation device, wherein the monitored temperature data is a temperature of the coolant such that proper functioning of the ablation device is determinable prior to use thereof in the ablation procedure so as to reduce a likelihood of an improper ablation during the ablation procedure.

2. The method of claim 1, wherein the power delivered to the ablation device is between 1 and 20 watts.

3. The method of claim 1, wherein the pre-ablation procedure comprises delivering the power to the ablation device for 5 to 30 seconds.

4. The method of claim 1, further comprising determining a power efficiency of the ablation device.

5. The method of claim 1, wherein the medium is sterilized water.

6. The method of claim 1, wherein the medium is a tissue to receive an ablation procedure.

7. The method of claim 1, further comprising conducting an ablation procedure.

8. The method of claim 1, wherein monitoring the temperature data included detecting variances, including rapid increases and sudden changes in temperature, to determine whether the ablation device is functioning properly.

9. The method of claim 8, wherein further comprising maintaining the device within a temperature range using the monitored temperature data.

10. The method of claim 1, wherein the pre-ablation procedure is performed using a pre-ablation procedure power level that is lower than the power level of the ablation procedure, and wherein the pre-ablation procedure power level is about 5 W.

11. A method of preparing an ablation device for an ablation procedure, the method comprising:
   inserting an ablation device into a medium;
   initiating a pre-ablation procedure before the ablation procedure, the pre-ablation procedure comprising:
      causing a coolant pump to deliver coolant to the ablation device;
      causing an ablation generator to provide power to the ablation device;
      monitoring a temperature of the coolant;
      monitoring power data representative of the power provided to the ablation device; and
   determining a condition of the ablation device based on the monitored temperature and monitored power data; and
      wherein the monitored temperature is the temperature of the coolant such that proper functioning of the ablation device is determinable prior to use thereof in the ablation procedure so as to reduce a likelihood of an improper ablation during the ablation procedure.

12. The method of claim 11, wherein the power delivered to the ablation device is between 1 and 20 watts.

13. The method of claim 11, wherein the pre-ablation procedure comprises delivering the power to the ablation device for 5 to 30 seconds.

14. The method of claim 11, further comprising determining a power efficiency of the ablation device.

15. The method of claim 11, wherein the medium is sterilized water.

16. The method of claim 11, wherein the medium is a tissue to receive an ablation procedure.

17. The method of claim 11, further comprising conducting an ablation procedure.

18. The method of claim 11, wherein further comprising maintaining the device within a temperature range using the monitored temperature.

19. A tissue ablation system comprising:
an ablation device configured to provide energy to a target area;
an ablation generator configured to provide power to the ablation device;
a controller in communication with the ablation generator and being configured to initiate a pre-ablation procedure before an ablation procedure, wherein during the pre-ablation procedure, the controller is configured to:
cause a coolant pump to deliver coolant to the ablation device;
cause an ablation generator to provide power to the ablation device;
monitor a temperature of the coolant;
monitor power data representative of the power provided to the ablation device; and
determine a condition of the ablation device based on the monitored temperature and monitored power data; and
providing a coolant to the ablation device, wherein the monitored temperature is the temperature of the coolant such that proper functioning of the ablation device is determinable prior to use thereof in the ablation procedure so as to reduce a likelihood of an improper ablation during the ablation procedure.

20. The tissue ablation system of claim 19, wherein further comprising maintaining the device within a temperature range using the monitored temperature.

* * * * *